(12) United States Patent
Huang et al.

(10) Patent No.: US 9,688,659 B2
(45) Date of Patent: Jun. 27, 2017

(54) DEUTERATED COMPOUNDS FOR TREATING HEMATOLOGIC MALIGNANCIES, AND COMPOSITIONS AND METHODS THEREOF

(71) Applicant: NeuForm Pharmaceuticals, Inc., Framingham, MA (US)

(72) Inventors: Chaoran Huang, Auburndale, MA (US); Changfu Cheng, Northborough, MA (US)

(73) Assignee: NeuForm Pharmaceuticals, Inc., Framingham, MA (US)

( * ) Notice: Subject to any disclaimer, the term of this patent is extended or adjusted under 35 U.S.C. 154(b) by 0 days.

(21) Appl. No.: 15/267,909

(22) Filed: Sep. 16, 2016

(65) Prior Publication Data

US 2017/0114041 A1 Apr. 27, 2017

Related U.S. Application Data

(60) Provisional application No. 62/244,267, filed on Oct. 21, 2015.

(51) Int. Cl.
| | |
|---|---|
| *C07D 401/14* | (2006.01) |
| *C07D 403/14* | (2006.01) |
| *A61K 31/53* | (2006.01) |
| *A61K 31/444* | (2006.01) |
| *A61K 35/00* | (2006.01) |
| *C07B 59/00* | (2006.01) |

(52) U.S. Cl.
CPC .......... *C07D 401/14* (2013.01); *A61K 31/444* (2013.01); *A61K 31/53* (2013.01); *C07B 59/002* (2013.01); *C07D 403/14* (2013.01); *C07B 2200/05* (2013.01)

(58) Field of Classification Search
CPC .... C07D 401/14; C07D 403/14; A61K 31/53; A61K 31/4444; A61K 31/444
USPC .......................................... 544/209; 514/245
See application file for complete search history.

(56) References Cited

U.S. PATENT DOCUMENTS

| | | | | |
|---|---|---|---|---|
| 6,221,335 B1* | 4/2001 | Foster | ................... | C07B 59/002 424/1.81 |
| 6,440,710 B1* | 8/2002 | Keinan | ................... | C12P 13/02 435/147 |
| 6,603,008 B1* | 8/2003 | Ando | ................... | C07D 405/14 546/269.7 |
| 7,517,990 B2* | 4/2009 | Ito | ................... | C07B 59/002 546/184 |
| 2007/0082929 A1* | 4/2007 | Gant | ................... | C07D 401/12 514/338 |
| 2007/0197695 A1* | 8/2007 | Potyen | ................... | C08K 5/55 524/110 |
| 2012/0196814 A1* | 8/2012 | Gong | ................... | C07H 15/26 514/25 |
| 2013/0190287 A1* | 7/2013 | Cianchetta | ......... | A61K 31/5377 514/210.2 |

FOREIGN PATENT DOCUMENTS

| | | |
|---|---|---|
| WO | 2015/003355 A2 | 1/2015 |
| WO | 2015/003360 A2 | 1/2015 |

OTHER PUBLICATIONS

Stein E.Y. Best Practice & Research Clinical Haematology 28 (2015) 112-115.*
Cairns et al., Cancer Discov; 3(7); 730-41, 2013.*
Krell et al., Future Oncol. (2013) 9(12), 1923-1935.*
Reitman et al., J Natl Cancer Inst 2010; 102: 932-941.*
Cecil Textbook of Medicine, edited by Bennet, J.C., and Plum F., 20th edition,vol. 1, 1004-1010, 1996.*
Dyck, Journal of Neurochemistry vol. 46 Issue 2, pp. 399-404 (1986).*
Tonn, Biological Mass Spectrometry vol. 22 Issue 11, pp. 633-642 (1993).*
Haskins, Biomedical Spectrometry vol. 9 Issue 7, pp. 269-277 (1982).*
Wolen, Journal of Clinical Pharmacology 1986; 26:419-424.*
Browne, Journal of Clinical Pharmacology1998; 38:213-220.*
Baillie, Pharmacology Rev.1981 ;33:81-132.*
Gouyette, Biomedical and Environmental Mass Spectrometry, vol. 15, 243-247 (1988).*
Cherrah, Biomedical and Environmental Mass Spectrometry vol. 14 Issue 11, pp. 653-657 (1987).*
Pieniaszek, J Clin Pharmacol.1999; 39:817-825.*
Honma et al., Drug Metab Dispos 15 (4): 551 (1987).*
Dang L., et al. Cancer-associated IDH1 mutations produce 2-hydroxyglutarate. Nature. 462(7274):739-44 (2009).
Gross S., et al. Cancer-associated metabolite 2-hydroxyglutarate accumulates in acute myelogenous leukemia with isocitrate dehydrogenase 1 and 2 mutations. J. Exp. Med. vol. 207 No. 2 339-344 (2010).
Ward PS, et al. The common feature of leukemia-associated IDH1 and IDH2 mutations is a neomorphic enzymatic activity that converts α-ketoglutarate to 2-hydroxyglutarate. Cancer Cell. 17(3):225-234 (2010).
Yen KE, et al. Cancer-associated IDH mutations: biomarker and therapeutic opportunities. Oncogene 29, 6409-6417 (2010).
Figueroa ME, et al. Leukemic IDH1 and IDH2 mutations result in a hypermethylation phenotype, disrupt TET2 function, and impair hematopoietic differentiation. Cancer Cell. Dec. 14, 2010; 18(6): 553-567.
Cairns RA, et al. Regulation of cancer cell metabolism. Nat Rev Cancer. Feb. 2011;11(2):85-95.
Patel KP, et al. Acute myeloid leukemia with IDH1 or IDH2 mutation Am J Clin Pathol 2011;135:35-45.
Darrell DR. et al. Frequent Mutation of Isocitrate Dehydrogenase (IDH)1 and IDH2 in Cholangiocarcinoma Identified Through Broad-Based Tumor Genotyping. The Oncologist 2012;17:72-79.
Yen KY, et al. Cancer-Associated Isocitrate Dehydrogenase Mutations The Oncologist 2012;17:5-8.
Koivunen P, et al. Transformation by the R Enantiomer of 2-Hydroxyglutarate Linked to EgIN Activation. Nature. ; 483(7390): 484-488.

(Continued)

*Primary Examiner* — Venkataraman Balasubramanian
(74) *Attorney, Agent, or Firm* — Milstein Zhang & Wu LLC

(57) ABSTRACT

The invention provides novel chemical compounds useful for treating various hematologic malignancies, or a related disease or disorder thereof, and pharmaceutical composition and methods of preparation and use thereof.

14 Claims, 5 Drawing Sheets

(56) References Cited

OTHER PUBLICATIONS

Sasaki M, et al. IDH1(R132H) mutation increases murine haematopoietic progenitors and alters epigenetics. Nature. Aug. 30, 2012; 488(7413): 656-659.
Sasaki M, et al. D-2-hydroxyglutarate produced by mutant IDH1 perturbs collagen maturation and basement membrane function. Genes & Development 26:2038-2049, 2012.
Kernytsky A, et al. IDH2 Mutation-induced histone and DNA hypermethylation is progressively reversed by small-molecule inhibition. Blood. 2015;125(2):296-303).
Davis MI, et al. Biochemical, Cellular and Biophysical Characterization of a Potent Inhibitor of Mutant Isocitrate Dehydrogenase IDH1. J. Biol. Chem. Mar. 25, 2014.
Hirata M, et al. Mutant IDH is sufficient to initiate enchondromatosis in mice. PNAS, Mar. 3, vol. 112, No. 9, p. 2833, 2015.
Yang H, et al. IDH1 and IDH2 Mutations in Tumorigenesis: Mechanistic Insights and Clinical Perspectives. Clin Cancer Res; 18(20) Oct. 15, 2012.

\* cited by examiner

US 9,688,659 B2

DEUTERATED COMPOUNDS FOR TREATING HEMATOLOGIC MALIGNANCIES, AND COMPOSITIONS AND METHODS THEREOF

PRIORITY CLAIMS AND RELATED PATENT APPLICATIONS

This application claims the benefit of priority from U.S. Provisional Application Ser. No. 62/244,267, filed on Oct. 21, 2015, the entire content of which is incorporated herein by reference in its entirety.

TECHNICAL FIELDS OF THE INVENTION

The invention generally relates to therapeutics and treatment methods for certain diseases and conditions. More particularly, the invention provides novel chemical compounds, with one or more deuterium-substitutions at strategic positions, useful for treating various hematologic malignancies and related diseases and conditions, and pharmaceutical compositions and methods of preparation and use thereof.

BACKGROUND OF THE INVENTION

Hematologic malignancies (a.k.a., blood cancer or liquid tumors) are forms of cancer that begin in the cells of blood-forming tissue, for example, the bone marrow or in the cells of the immune system. Examples of hematologic cancers include acute and chronic leukemia, lymphomas, multiple myeloma and myelodysplastic syndromes.

Leukemia is a type of cancer that occurs in the bone marrow and in the blood. There are two types of leukemia: Lymphocytic leukemia involves lymphocytes. Myelogenous leukemia involves granulocytes. These white blood cells are important in fight infections. Lymphoma is a type of cancer that develops in the lymphatic system. There are two general types of lymphoma depending on how cancer spreads. In Hodgkin lymphoma, the cancer spreads from one group of lymph nodes to another in a certain order. In non-Hodgkin lymphoma, the cancer spreads from one group of lymph nodes to another in a random order. Myeloma is a cancer that causes the plasma cells to form a tumor in the bone marrow. Myeloma is usually found in multiple places in the body, thus often called multiple myeloma.

Treatment of hematologic malignancies includes "watchful waiting" (e.g., in chronic lymphoid leukemia or CLL) or symptomatic treatment (e.g., blood transfusions in myelodysplastic syndromes or MDS). More aggressive forms of disease require treatment with chemotherapy, radiotherapy, immunotherapy or a bone marrow transplant. For example, rituximab, a chimeric monoclonal antibody against the protein CD20, is used to treat B-cell-derived hematologic malignancies, including follicular lymphoma and diffuse large B-cell lymphoma.

Isocitrate dehydrogenases are metabolic enzymes that are mutated in a wide range of hematologic and solid tumor malignancies, including acute myelogenous leukemia and glioma, a type of aggressive brain tumor with poor prognosis. Normally, IDH enzymes help to break down nutrients and generate energy for cells. Mutations in the IDH genes are strongly correlated with the development of acute myelogenous leukemia, glioma, chondrosarcoma, intrahepatic cholangiocarcinoma, and angioimmunoblastic T-cell lymphoma cancers. They also cause D-2-hydroxyglutaric aciduria and Ollier and Maffucci syndromes.

Hematologic and solid malignancies are placing an increasing burden on society, impairing the health and lives of those affected. Although medications have been developed to treat some of these diseases and conditions, the available treatments are often limited in terms of clinical effectiveness and at the same time have undesirable side effects.

There is an urgent and growing need for innovative therapeutics and treatment methods that provide improved clinical effectiveness with reduced side effects.

SUMMARY OF THE INVENTION

The invention provides novel, orally available, selective and potent inhibitors of mutated IDH2 protein. They specifically inhibit IDH2 in the mitochondria, which inhibit the formation of 2-hydroxyglutarate (2HG), resulting in both an induction of cellular differentiation and an inhibition of cellular proliferation in IDH2-expressing tumor cells. Thus, the compounds of the invention are highly targeted agents for the treatment of patients with cancers that harbor an IDH2 mutation.

In one aspect, the invention generally relates to a compound having the structural formula of:

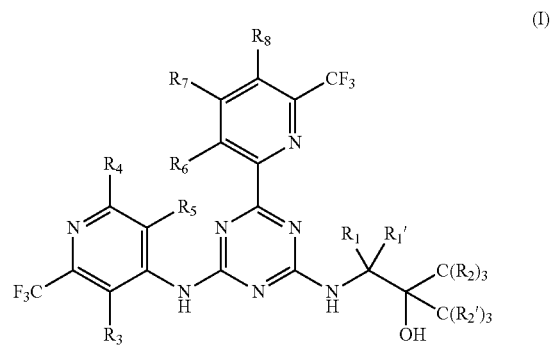

(I)

wherein each of $R_1$, $R_{1'}$, $R_2$, $R_{2'}$, $R_3$, $R_4$, $R_5$, $R_6$, $R_7$ and $R_8$ is independently selected from H and D; provided that at least one of $R_1$, $R_{1'}$, $R_2$, $R_{2'}$, $R_3$, $R_4$, $R_5$, $R_6$, $R_7$ and $R_8$ is D, or a pharmaceutically acceptable form thereof.

In another aspect, the invention generally relates to a compound having the structural formula of:

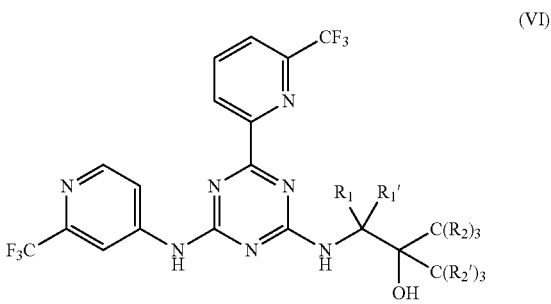

(VI)

wherein each of $R_1$, $R_{1'}$, $R_2$ and $R_{2'}$ is independently selected from H and D; provided that at least one of $R_1$, $R_{1'}$, $R_2$ and $R_{2'}$ is D, or a pharmaceutically acceptable form thereof.

In yet another aspect, the invention generally relates to a pharmaceutical composition comprising a compound having the structural formula of:

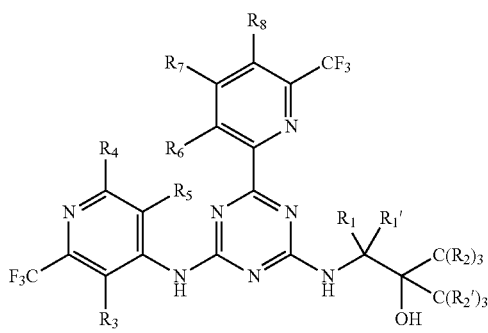

(I)

wherein each of $R_1$, $R_{1'}$, $R_2$, $R_{2'}$, $R_3$, $R_4$, $R_5$, $R_6$, $R_7$ and $R_8$ is independently selected from H and D; provided that at least one of $R_1$, $R_{1'}$, $R_2$, $R_{2'}$, $R_3$, $R_4$, $R_5$, $R_6$, $R_7$ and $R_8$ is D, or a pharmaceutically acceptable form thereof, effective to treat, prevent, or reduce one or more hematologic malignancies, or a related disease or disorder thereof, in a mammal, including a human, and a pharmaceutically acceptable excipient, carrier, or diluent.

In yet another aspect, the invention generally relates to a pharmaceutical composition comprising a compound having the structural formula of:

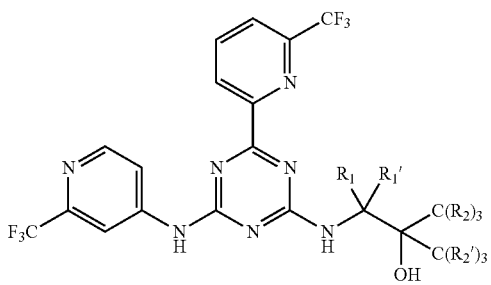

(VI)

wherein each of $R_1$, $R_{1'}$, $R_2$ and $R_{2'}$ is independently selected from H and D; provided that at least one of $R_1$, $R_{1'}$, $R_2$ and $R_{2'}$ is D, or a pharmaceutically acceptable form thereof, effective to treat, prevent, or reduce one or more hematologic malignancies, or a related disease or disorder thereof, in a mammal, including a human, and a pharmaceutically acceptable excipient, carrier, or diluent.

In yet another aspect, the invention generally relates to a unit dosage form comprising the pharmaceutical composition disclosed herein. The unit dosage is suitable for administration to a subject suffering from one or more hematologic malignancies, including advanced hematologic malignancies, or a related disease or disorder thereof.

In yet another aspect, the invention generally relates to a method for treating, reducing, or preventing a disease or disorder. The method includes: administering to a subject in need thereof a pharmaceutical composition comprising a compound having the formula of:

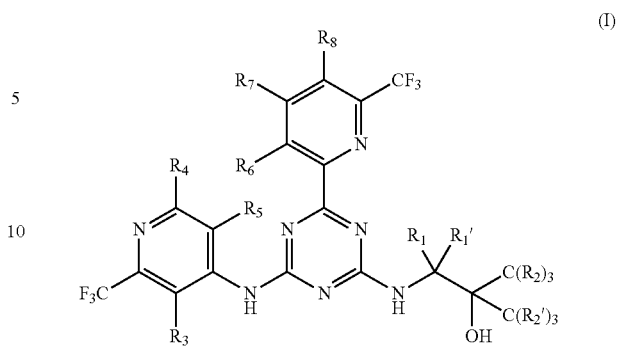

(I)

wherein each of $R_1$, $R_{1'}$, $R_2$, $R_{2'}$, $R_3$, $R_4$, $R_5$, $R_6$, $R_7$ and $R_8$ is independently selected from H and D; provided that at least one of $R_1$, $R_{1'}$, $R_2$, $R_{2'}$, $R_3$, $R_4$, $R_5$, $R_6$, $R_7$ and $R_8$ is D, or a pharmaceutically acceptable form thereof, effective to treat, prevent, or reduce one or more hematologic malignancies, or related a related disease or disorder thereof.

In yet another aspect, the invention generally relates to a method for treating, reducing, or preventing a disease or disorder. The method includes: administering to a subject in need thereof a pharmaceutical composition comprising a compound having the formula of:

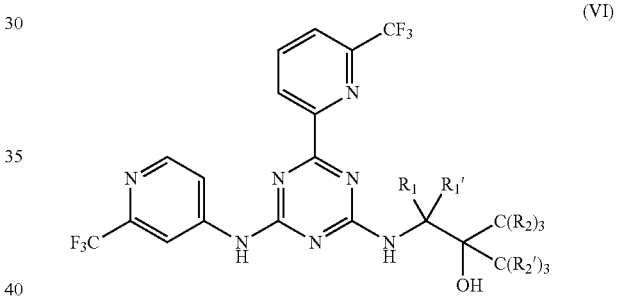

(VI)

wherein each of $R_1$, $R_{1'}$, $R_2$ and $R_{2'}$ is independently selected from H and D; provided that at least one of $R_1$, $R_{1'}$, $R_2$ and $R_{2'}$ is D, or a pharmaceutically acceptable form thereof, effective to treat, prevent, or reduce one or more hematologic malignancies, or a related disease or disorder thereof.

DEFINITIONS

Figure 1:
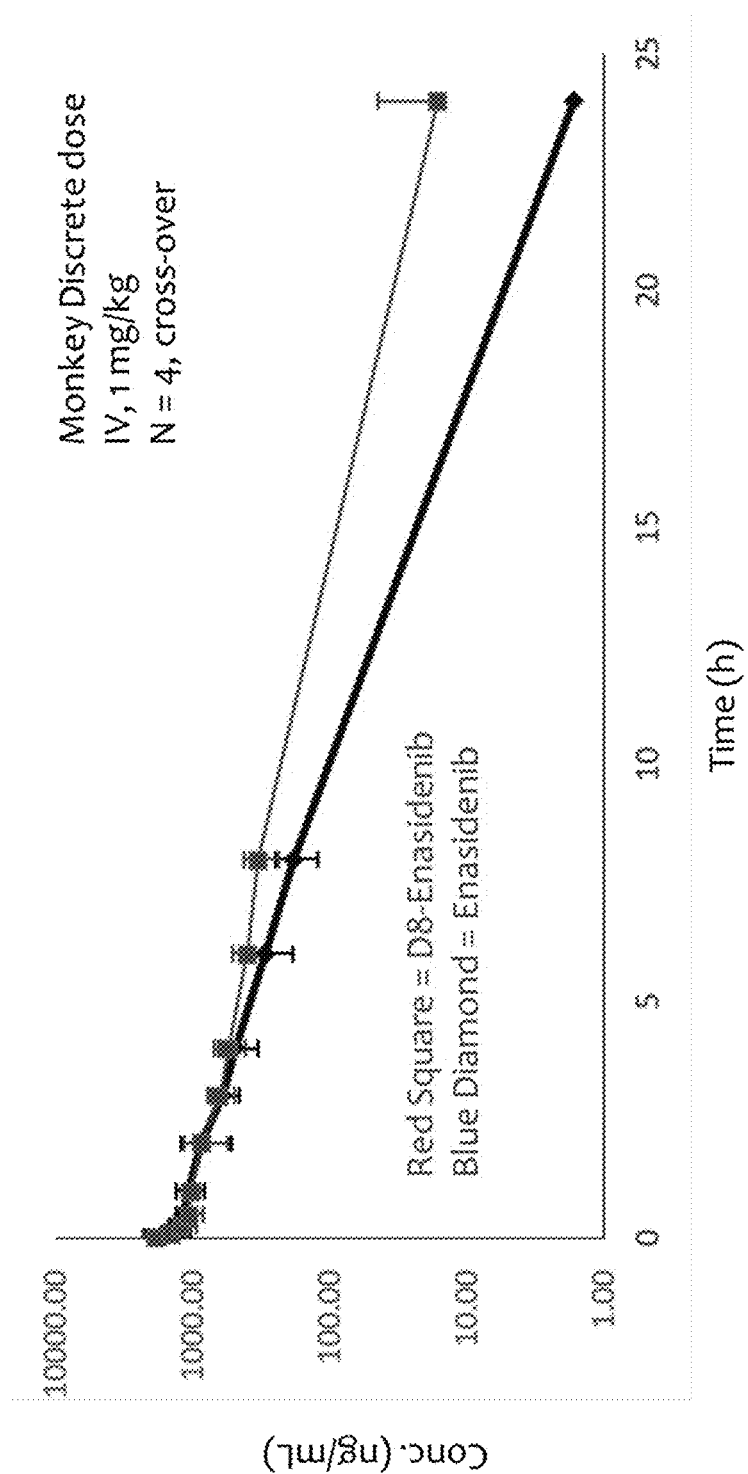
FIG. 1 shows exemplary monkey intravenous studies on pharmacokinetics of enasidenib and D8-enasidenib.

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

As used herein, "administration" of a disclosed compound encompasses the delivery to a subject of a compound as described herein, or a prodrug or other pharmaceutically acceptable derivative thereof, using any suitable formulation or route of administration, as discussed herein.

As used herein, the terms "effective amount" or "therapeutically effective amount" refer to that amount of a compound or pharmaceutical composition described herein that is sufficient to effect the intended application including, but not limited to, disease treatment, as illustrated herein. In some embodiments, for example, the amount is that effective for detectable killing or inhibition of the growth or spread of cancer cells; the size or number of tumors; or other measure of the level, stage, progression or severity of the cancer. The therapeutically effective amount can vary depending upon the intended application, or the subject and disease condition being treated, e.g., the desired biological endpoint, the pharmacokinetics of the compound, the disease being treated, the mode of administration, and the weight and age of the patient, which can readily be determined by one of ordinary skill in the art. The term also applies to a dose that will induce a particular response in target cells, e.g., reduction of cell migration. The specific dose will vary depending on, for example, the particular compounds chosen, the species of subject and their age/existing health conditions or risk for health conditions, the dosing regimen to be followed, the severity of the disease, whether it is administered in combination with other agents, timing of administration, the tissue to which it is administered, and the physical delivery system in which it is carried.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. Treatment is aimed to obtain beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

As used herein, the term "therapeutic effect" refers to a therapeutic benefit and/or a prophylactic benefit as described herein. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the term "pharmaceutically acceptable ester" refers to esters that hydrolyze in vivo and include those that break down readily in the human body to leave the parent compound or a salt thereof. Such esters can act as a prodrug as defined herein. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfinic acids, sulfonic acids and boronic acids. Examples of esters include formates, acetates, propionates, butyrates, acrylates and ethylsuccinates. The esters can be formed with a hydroxy or carboxylic acid group of the parent compound.

As used herein, the term "pharmaceutically acceptable enol ethers" include, but are not limited to, derivatives of formula —C═C(OR) where R can be selected from alkyl, alkenyl, alkynyl, aryl, aralkyl and cycloalkyl. Pharmaceutically acceptable enol esters include, but are not limited to, derivatives of formula —C═C(OC(O)R) where R can be selected from hydrogen, alkyl, alkenyl, alkynyl, aryl, aralkyl and cycloalkyl.

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds. In one embodiment, a "pharmaceutically acceptable form" includes, but is not limited to, pharmaceutically acceptable salts, isomers, prodrugs and isotopically labeled derivatives of disclosed compounds. In some embodiments, a "pharmaceutically acceptable form" includes, but is not limited to, pharmaceutically acceptable salts, stereoisomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. *Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchioric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)^4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein, the "low dosage" generally refers to at least 5% less (e.g., at least 10%, 20%, 50%, 80%, 90%, or even 95%) than the lowest standard recommended dosage of a particular compound formulated for a given route of administration for treatment of any human disease or condition. By way of an example, a low dosage of an agent that reduces glucose levels and that is formulated for administration by inhalation will differ from a low dosage of the same agent formulated for oral administration.

As used herein, the "high dosage" is generally meant at least 5% (e.g., at least 10%, 20%, 50%, 100%, 200%, or even 300%) more than the highest standard recommended dosage of a particular compound for treatment of any human disease or condition.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates and polymorphs of the compounds of the invention are also contemplated herein. Solvates of the compounds of the present invention include, for example, hydrates.

DETAILED DESCRIPTION OF THE INVENTION

The invention provides novel chemical entities that are biochemically potent and physiologically active with improved pharmacokinetic and toxicological properties and anti-cancer bioactivity over the compound enasidenib, shown below.

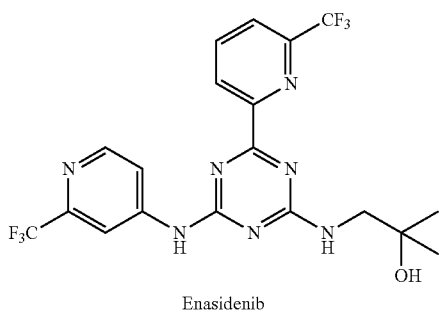

Enasidenib

The compounds disclosed herein are deuterium-substituted versions of the above compound, where hydrogen is substituted with deuterium at strategic locations of the molecule. The substitution locations are selected with the specific objective to impact pharmacokinetic and toxicological properties of the molecule. The resulting compounds have 1 to 8 deuterium substitutions and exhibit more desirable profiles in terms of safety, efficacy and tolerability in the treatment of hematologic malignancies and related diseases and conditions, including acute myelogenous leukemia (AML), myelodysplasia syndrome (MDS), myeloproliferative neoplasms (MPN), myeloproliferative neoplasms (MPN), chronic myelomonocytic leukemia (CMML), B-acute lymphoblastic leukemia (B-ALL), B-acute lymphoblastic leukemia (B-ALL), or lymphoma (e.g., T-cell lymphoma), each characterized by the presence of a mutant allele of IDH1.

Isocitrate dehydrogenase (IDH) types 1 and 2 are metabolic enzymes that are mutated in a wide range of hematologic and solid tumor malignancies, including AML, and glioma (a type of aggressive brain tumor). Normally, IDH enzymes help to break down nutrients and generate energy for cells. When mutated, IDH creates a molecule that alters the cells' genetic programming, and instead of maturing, the cells remain primitive and proliferate quickly.

Isocitrate dehydrogenase type 2 (IDH2) is an enzyme in the citric acid cycle and is mutated in a variety of cancers. It initiates and drives cancer growth by blocking differentiation and the production of the oncometabolite 2HG.

The compounds disclosed herein are orally available, selective and potent inhibitors of mutated IDH2 protein. They specifically inhibit IDH2 in the mitochondria, which inhibit the formation of 2-hydroxyglutarate, resulting in both an induction of cellular differentiation and an inhibition of cellular proliferation in IDH2-expressing tumor cells. Thus, the compounds of the invention are highly targeted agents for the treatment of patients with cancers that harbor an IDH2 mutation.

In one aspect, the invention generally relates to a compound having the structural formula of:

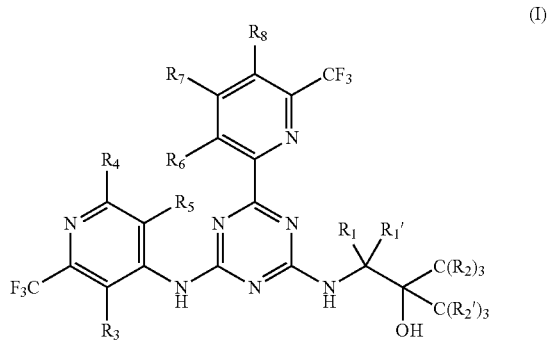

wherein each of $R_1$, $R_{1'}$, $R_2$, $R_{2'}$, $R_3$, $R_4$, $R_5$, $R_6$, $R_7$ and $R_8$ is independently selected from H and D; provided that at least one of $R_1$, $R_{1'}$, $R_2$, $R_{2'}$, $R_3$, $R_4$, $R_5$, $R_6$, $R_7$ and $R_8$ is D, or a pharmaceutically acceptable form thereof.

In certain embodiments of (I), one of $R_1$ and $R_{1'}$ is D. In certain embodiments of (I), each of $R_1$ and $R_{1'}$ is D.

In certain embodiments of (I), one of $R_2$ and $R_{2'}$ is D. In certain embodiments of (I), each of $R_2$ and $R_{2'}$ is D.

In certain embodiments of (I), each of $R_1$ and $R_{1'}$ is D and each of $R_2$ and $R_{2'}$ is H, having the structural formula of:

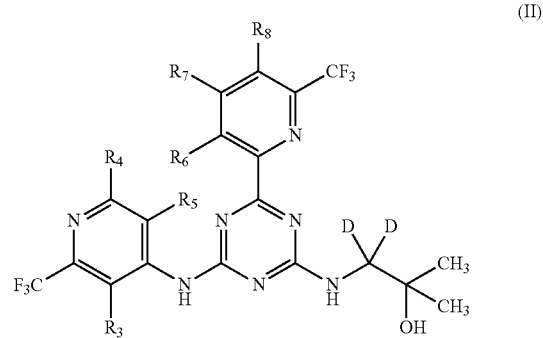

TABLE 1

Examples of Formula (II)

| Compound # | $R_{1,1'}$ | $R_{2,2'}$ | $R_3$ | $R_4$ | $R_5$ | $R_6$ | $R_7$ | $R_8$ |
|---|---|---|---|---|---|---|---|---|
| 1 | D | H | H | H | H | H | H | H |
| 2 | D | H | D | H | H | H | H | H |
| 3 | D | H | H | D | H | H | H | H |
| 4 | D | H | H | H | D | H | H | H |
| 5 | D | H | D | D | D | H | H | H |
| 6 | D | H | D | H | H | D | D | D |
| 7 | D | H | H | D | H | D | D | D |
| 8 | D | H | H | H | D | D | D | D |
| 9 | D | H | D | D | D | H | D | H |
| 10 | D | H | D | D | D | H | D | H |
| 11 | D | H | D | D | D | H | H | D |
| 12 | D | H | H | H | H | D | H | H |
| 13 | D | H | H | H | H | H | D | H |

TABLE 1-continued

Examples of Formula (II)

| Compound # | $R_{1,1'}$ | $R_{2,2'}$ | $R_3$ | $R_4$ | $R_5$ | $R_6$ | $R_7$ | $R_8$ |
|---|---|---|---|---|---|---|---|---|
| 14 | D | H | H | H | H | H | H | D |
| 15 | D | H | H | H | H | D | D | D |

Exemplary structures of compounds of Table 1:

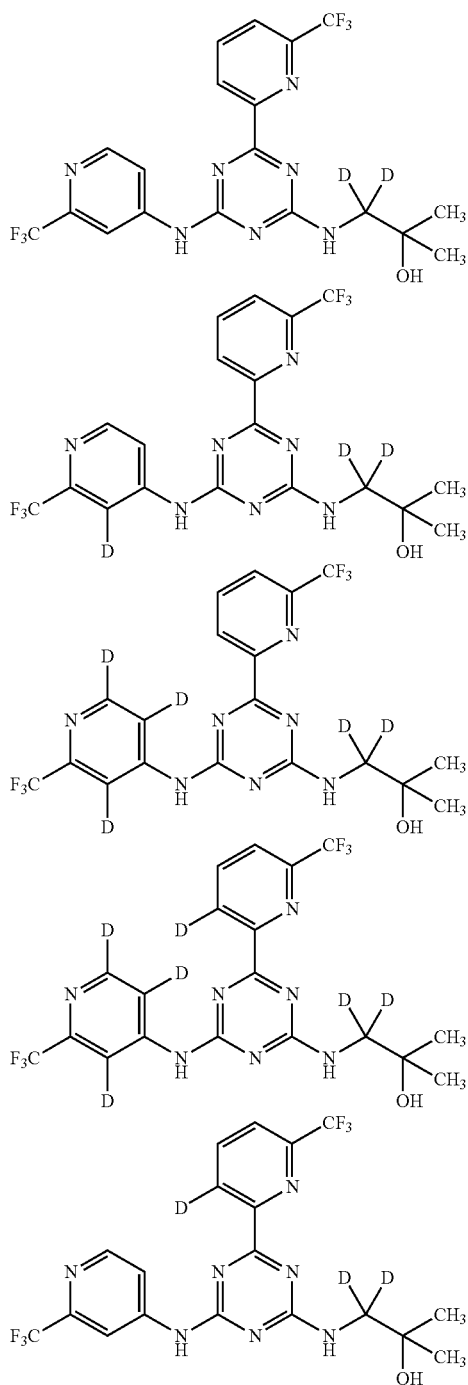

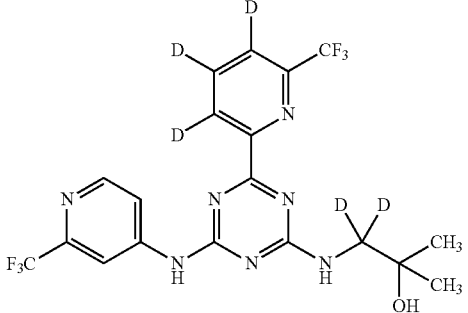

In certain embodiments of (I), each of $R_1$ and $R_{1'}$ is H and each of $R_2$ and $R_{2'}$ is D, having the structural formula of:

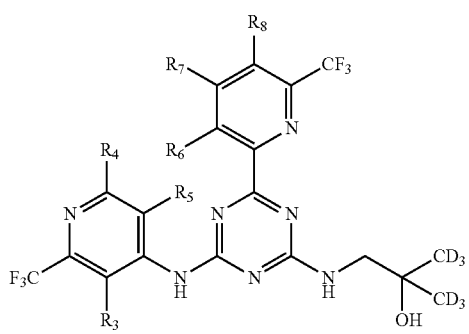

(III)

TABLE 2

Examples of Formula (III)

| Compound # | $R_{1,1'}$ | $R_{2,2'}$ | $R_3$ | $R_4$ | $R_5$ | $R_6$ | $R_7$ | $R_8$ |
|---|---|---|---|---|---|---|---|---|
| 16 | H | D | H | H | H | H | H | H |
| 17 | H | D | D | H | H | H | H | H |
| 18 | H | D | H | D | H | H | H | H |
| 19 | H | D | H | H | D | H | H | H |
| 20 | H | D | D | D | D | H | H | H |
| 21 | H | D | D | H | H | D | D | D |
| 22 | H | D | H | D | H | D | D | D |
| 23 | H | D | H | H | D | D | D | D |
| 24 | H | D | D | D | D | D | H | H |
| 25 | H | D | D | D | D | H | D | H |
| 26 | H | D | D | D | D | H | H | D |
| 27 | H | D | H | H | H | D | H | H |
| 28 | H | D | H | H | H | H | D | H |
| 29 | H | D | H | H | H | H | H | D |
| 30 | H | D | H | H | H | D | D | D |

Exemplary structures of compounds of Table 2:

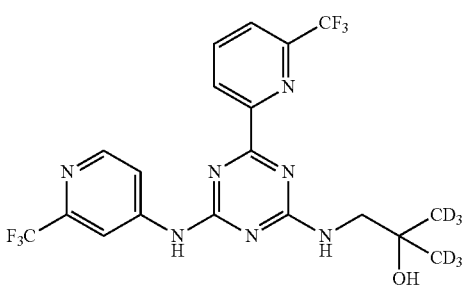

-continued
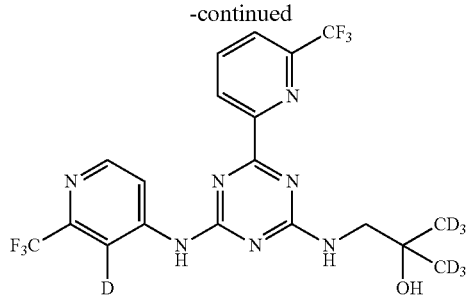
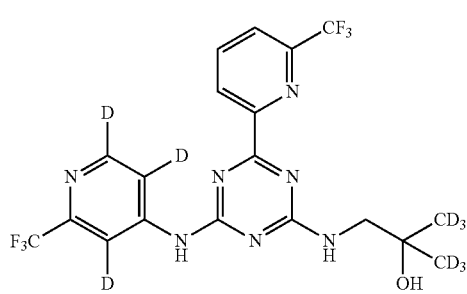
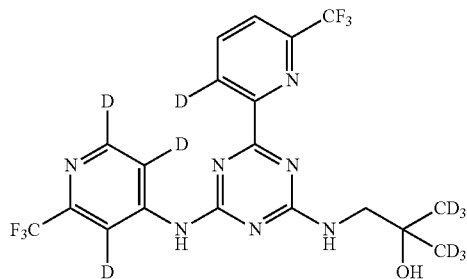
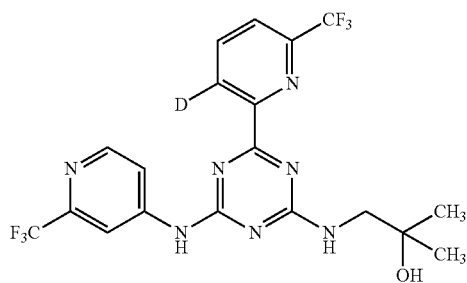
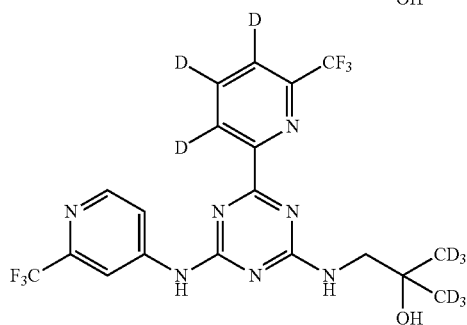
In certain embodiments of (I), each of and $R_{2'}$ is D, having the structural formula of:
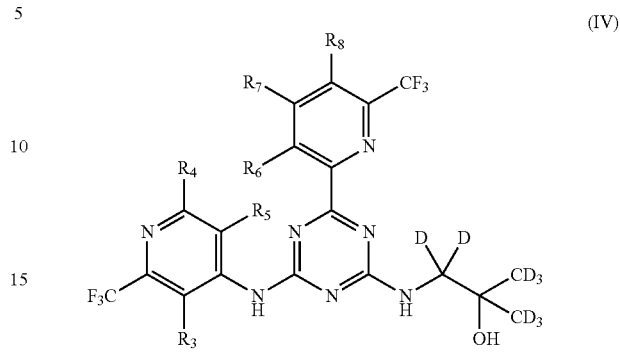
(IV)
TABLE 3
Examples of Formula (IV)
| Compound # | $R_{1,1'}$ | $R_{2,2'}$ | $R_3$ | $R_4$ | $R_5$ | $R_6$ | $R_7$ | $R_8$ |
|---|---|---|---|---|---|---|---|---|
| 31 | D | D | H | H | H | H | H | H |
| 32 | D | D | D | H | H | H | H | H |
| 33 | D | D | H | D | H | H | H | H |
| 34 | D | D | H | H | D | H | H | H |
| 35 | D | D | D | D | D | H | H | H |
| 36 | D | D | H | D | H | D | D | D |
| 37 | D | D | H | D | H | D | D | D |
| 38 | D | D | H | H | D | D | D | D |
| 39 | D | D | D | D | D | D | H | H |
| 40 | D | D | D | D | D | H | D | H |
| 41 | D | D | D | D | D | H | H | D |
| 42 | D | D | H | H | H | D | H | H |
| 43 | D | D | H | H | H | H | D | H |
| 44 | D | D | H | H | H | H | H | D |
| 45 | D | D | H | H | H | D | D | D |
Exemplary structures of compounds of Table 3:

-continued
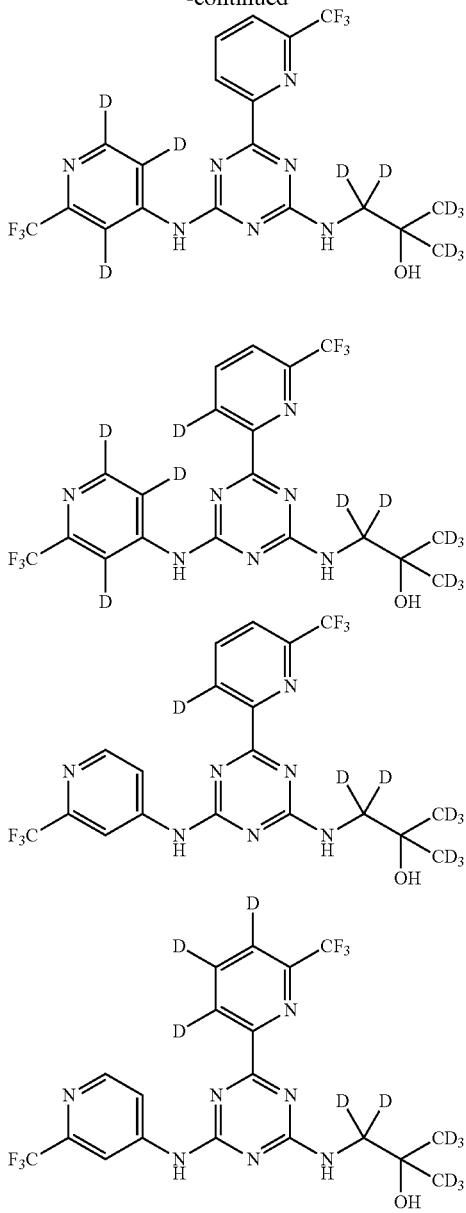
In certain embodiments of (I), each of $R_1$, $R_{1'}$, $R_2$ and $R_{2'}$ is H, having the structural formula of:
(V)
TABLE 4
Examples of Formula (V)
| Compound # | $R_{1,1'}$ | $R_{2,2'}$ | $R_3$ | $R_4$ | $R_5$ | $R_6$ | $R_7$ | $R_8$ |
|---|---|---|---|---|---|---|---|---|
| 46 | H | H | D | H | H | H | H | H |
| 47 | H | H | H | D | H | H | H | H |
| 48 | H | H | H | H | D | H | H | H |
| 49 | H | H | D | D | D | H | H | H |
| 50 | H | H | D | H | H | D | D | D |
| 51 | H | H | H | D | H | D | D | D |
| 52 | H | H | D | D | D | D | D | D |
| 53 | H | H | D | D | D | D | H | H |
| 54 | H | H | D | D | D | H | D | H |
| 55 | H | H | D | D | D | H | H | D |
| 56 | H | H | H | H | H | D | H | H |
| 57 | H | H | H | H | H | H | D | H |
| 58 | H | H | H | H | H | H | H | D |
| 59 | H | H | H | H | H | D | D | D |
Exemplary structures of compounds of Table 4:
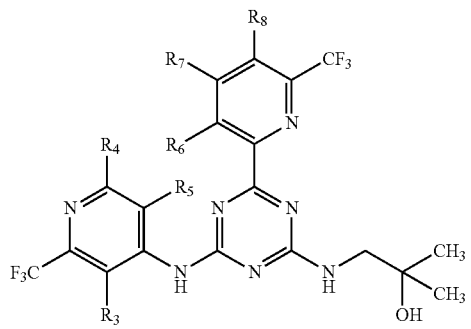

-continued

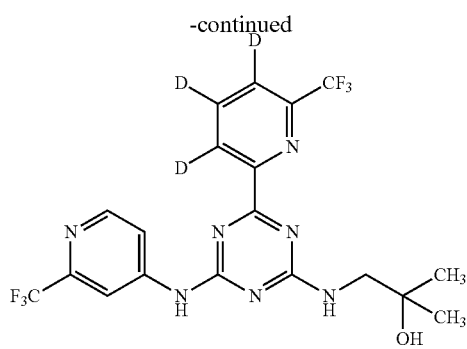

In another aspect, the invention generally relates to a compound having the structural formula of:

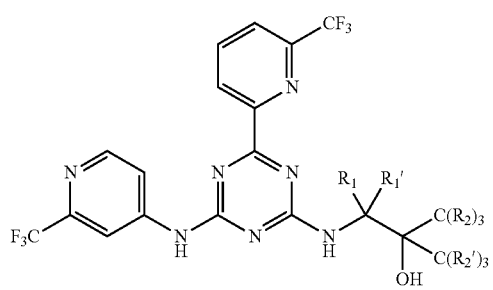
(VI)

wherein each of $R_1$, $R_{1'}$, $R_2$ and $R_{2'}$ is independently selected from H and D; provided that at least one of $R_1$, $R_{1'}$, $R_2$ and $R_{2'}$ is D, or a pharmaceutically acceptable form thereof.

In certain embodiment, the compound has the structural formula of:

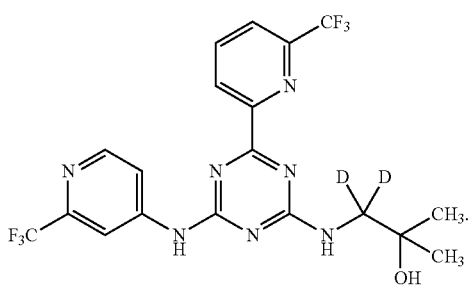

In certain embodiment, the compound has the structural formula of:

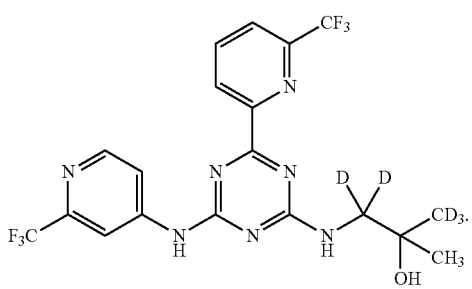

In certain embodiment, the compound has the structural formula of:

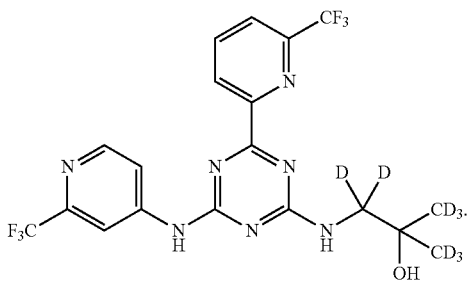

In certain embodiment, the compound has the structural formula of:

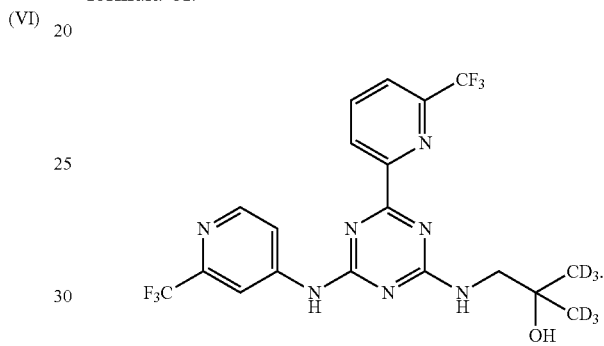

In certain embodiment, the compound has the structural formula of:

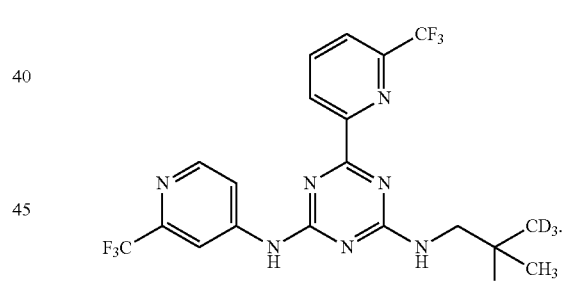

In certain embodiment, the compound has the structural formula of:

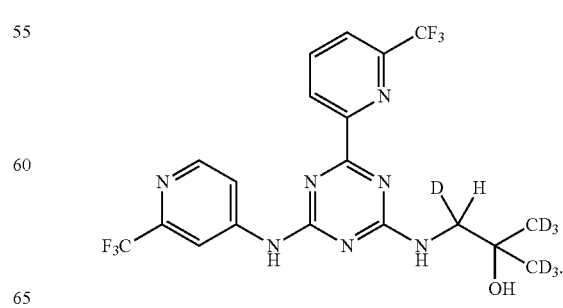

In certain embodiment, the compound has the structural formula of:

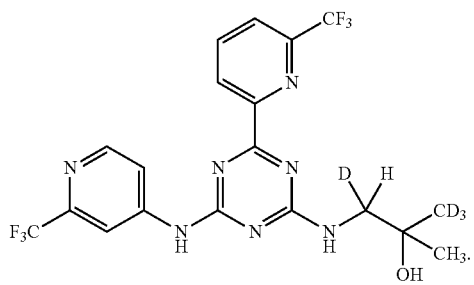

In certain embodiment, the compound has the structural formula of:

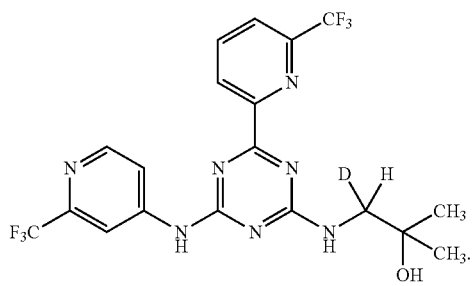

In yet another aspect, the invention generally relates to a pharmaceutical composition comprising a compound having the structural formula of:

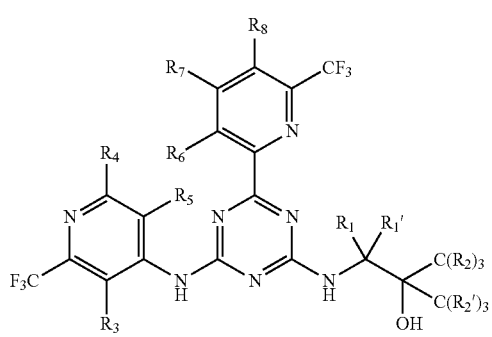

(I)

wherein each of $R_1$, $R_{1'}$, $R_2$, $R_{2'}$, $R_3$, $R_4$, $R_5$, $R_6$, $R_7$ and $R_8$ is independently selected from H and D; provided that at least one of $R_1$, $R_{1'}$, $R_2$, $R_{2'}$, $R_3$, $R_4$, $R_5$, $R_6$, $R_7$ and $R_8$ is D, or a pharmaceutically acceptable form thereof, effective to treat, prevent, or reduce one or more hematologic malignancies, or a related disease or disorder thereof, in a mammal, including a human, and a pharmaceutically acceptable excipient, carrier, or diluent.

In certain embodiments of the pharmaceutical composition, each of $R_1$ and $R_{1'}$ is D and each of $R_2$ and $R_{2'}$ is H, with the compound having the structural formula of:

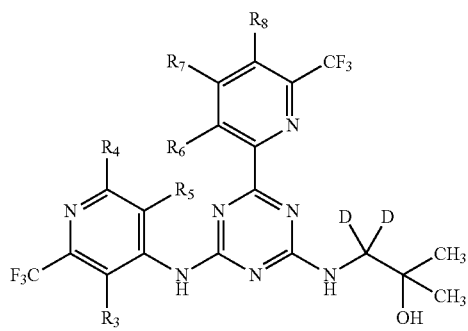

(II)

In certain embodiments of the pharmaceutical composition, each of $R_1$ and $R_{1'}$ is H and each of $R_2$ and $R_{2'}$ is D, with the compound having the structural formula of:

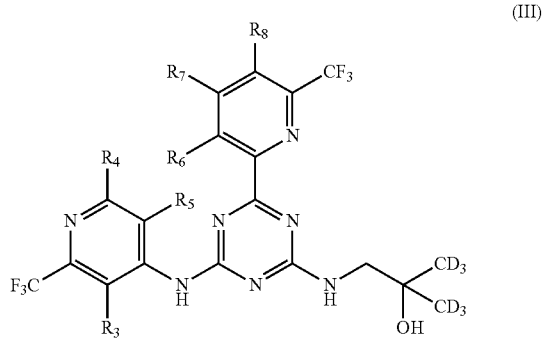

(III)

In certain embodiments of the pharmaceutical composition, each of $R_1$, $R_{1'}$, $R_2$ and $R_{2'}$ is D, with the compound having the structural formula of:

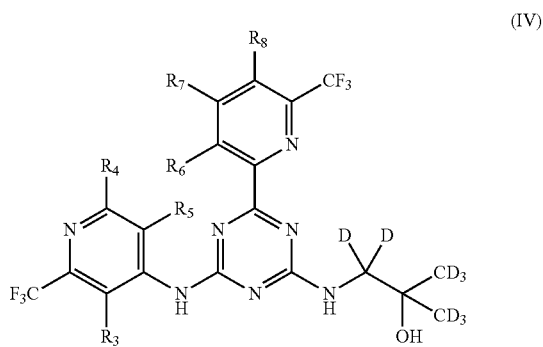

(IV)

In certain embodiments of the pharmaceutical composition, each of $R_1$, $R_{1'}$, $R_2$ and $R_{2'}$ is H, with the compound having the structural formula of:

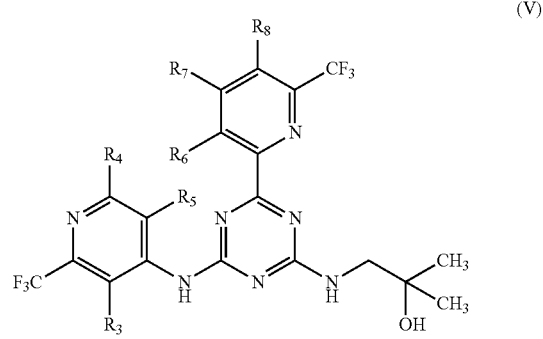

(V)

In yet another aspect, the invention generally relates to a pharmaceutical composition comprising a compound having the structural formula of:

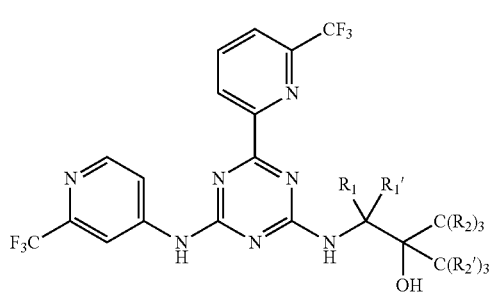

(VI)

wherein each of $R_1$, $R_{1'}$, $R_2$ and $R_{2'}$ is independently selected from H and D; provided that at least one of $R_1$, $R_{1'}$, $R_2$ and $R_{2'}$ is D, or a pharmaceutically acceptable form thereof, effective to treat, prevent, or reduce one or more hematologic malignancies, or a related disease or disorder thereof, in a mammal, including a human, and a pharmaceutically acceptable excipient, carrier, or diluent.

In certain embodiment of the pharmaceutical composition, the compound has the structural formula of:

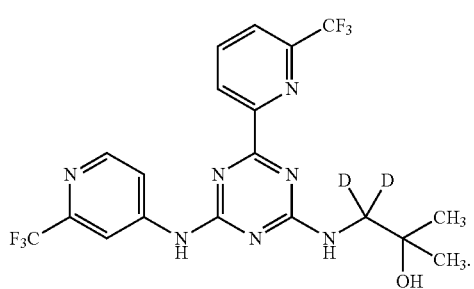

In certain embodiment of the pharmaceutical composition, the compound has the structural formula of:

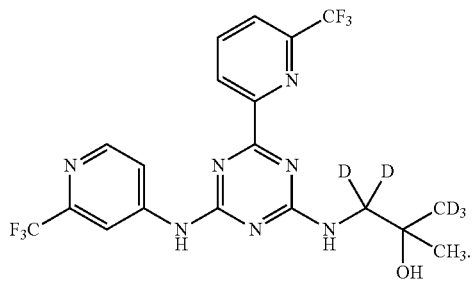

In certain embodiment of the pharmaceutical composition, the compound has the structural formula of:

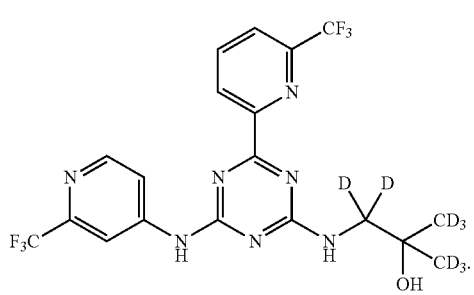

In certain embodiment of the pharmaceutical composition, the compound has the structural formula of:

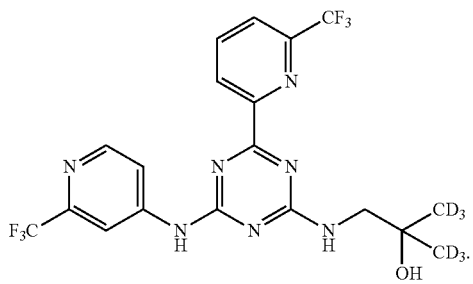

In certain embodiment of the pharmaceutical composition, the compound has the structural formula of:

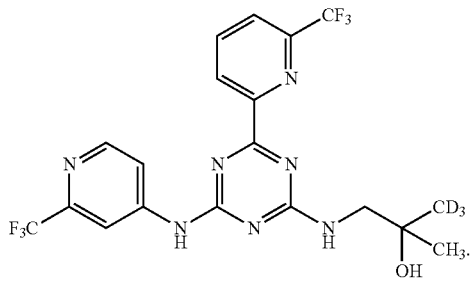

In certain embodiment of the pharmaceutical composition, the compound has the structural formula of:

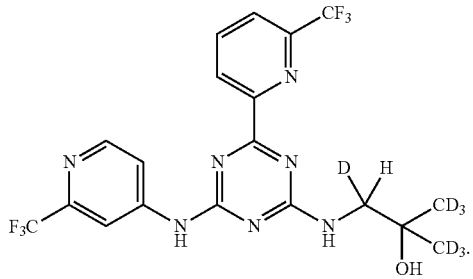 [SMILES: [2H]C([2H])([2H])C(O)(C([2H])([2H])[2H])C([2H])([2H])Nc1nc(Nc2ccnc(C(F)(F)F)c2)nc(-c2cccc(C(F)(F)F)n2)n1]

In certain embodiment of the pharmaceutical composition, the compound has the structural formula of:

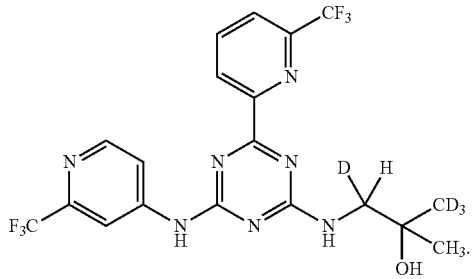

In certain embodiment of the pharmaceutical composition, the compound has the structural formula of:

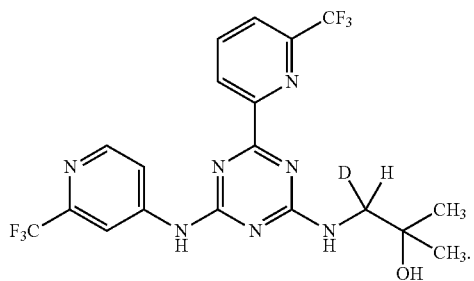

In yet another aspect, the invention generally relates to a unit dosage form comprising a pharmaceutical composition disclosed herein. The unit dosage form is suitable for administration to a subject suffering from one or more hematologic malignancies, including advanced hematologic malignancies, or a related disease or disorder thereof.

In yet another aspect, the invention generally relates to a method for treating, reducing, or preventing a disease or disorder. The method includes: administering to a subject in need thereof a pharmaceutical composition comprising compound having the formula of:

(I)

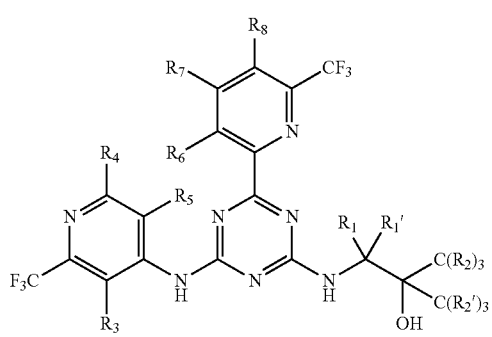

wherein each of $R_1$, $R_{1'}$, $R_2$, $R_{2'}$, $R_3$, $R_4$, $R_5$, $R_6$, $R_7$ and $R_8$ is independently selected from H and D; provided that at least one of $R_1$, $R_{1'}$, $R_2$, $R_{2'}$, $R_3$, $R_4$, $R_5$, $R_6$, $R_7$ and $R_8$ is D, or a pharmaceutically acceptable form thereof, effective to treat, prevent, or reduce one or more hematologic malignancies, including advanced hematologic malignancies, or related a related disease or disorder thereof.

In certain embodiments of the method for treating, reducing, or preventing a disease or disorder, each of $R_1$ and $R_{1'}$ is D and each of $R_2$ and $R_{2'}$ is H, with the compound having the structural formula of:

(II)

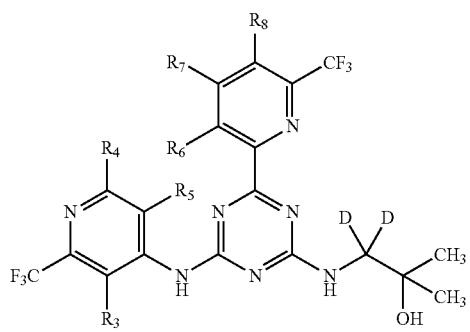

In certain embodiments of the method for treating, reducing, or preventing a disease or disorder, each of $R_1$ and $R_{1'}$ is H and each of $R_2$ and $R_{2'}$ is D, with the compound having the structural formula of:

(III)

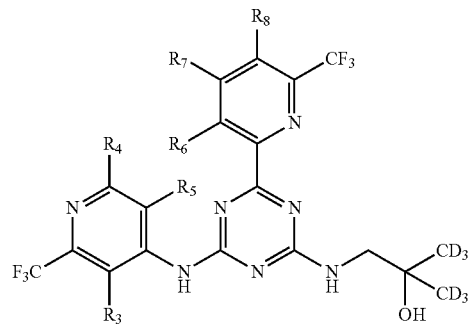

In certain embodiments of the method for treating, reducing, or preventing a disease or disorder, each of $R_1$, $R_{1'}$, $R_2$ and $R_{2'}$ is D, with the compound having the structural formula of:

(IV)

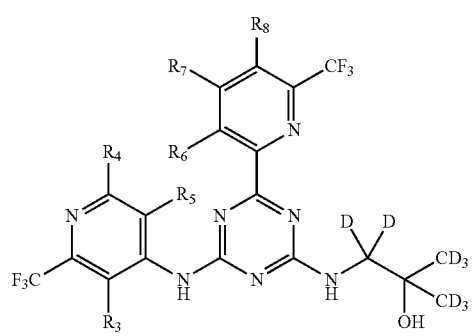

In certain embodiments of the method for treating, reducing, or preventing a disease or disorder, each of $R_1$, $R_{1'}$, $R_2$ and $R_{2'}$ is H, with the compound having the structural formula of:

(V)

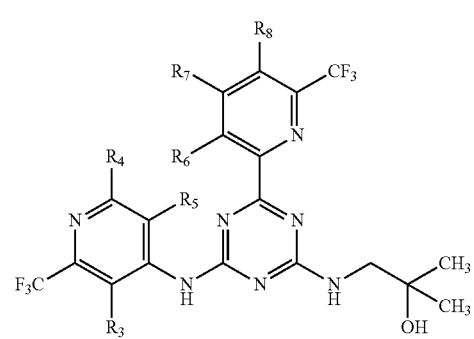

In yet another aspect, the invention generally relates to a method for treating, reducing, or preventing a disease or disorder. The method includes: administering to a subject in need thereof a pharmaceutical composition comprising compound having the formula of:

(VI)

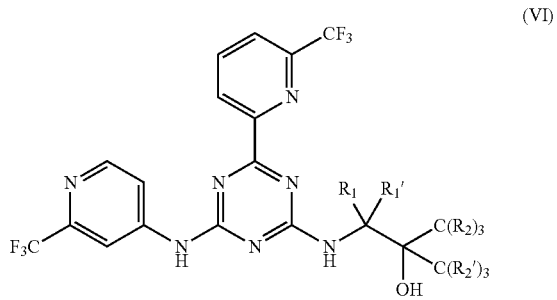

wherein each of $R_1$, $R_{1'}$, $R_2$ and $R_{2'}$ is independently selected from H and D; provided that at least one of $R_1$, $R_{1'}$, $R_2$ and $R_{2'}$ is D, or a pharmaceutically acceptable form thereof, effective to treat, prevent, or reduce one or more hematologic malignancies, including advanced hematologic malignancies, or related a related disease or disorder thereof.

In certain embodiment of the method, the compound has the structural formula of:

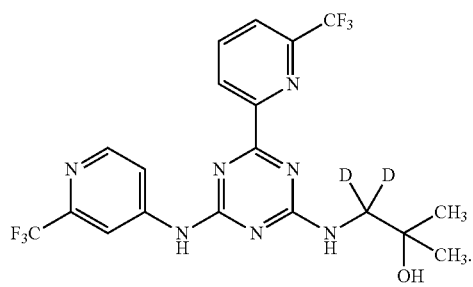

In certain embodiment of the method, the compound has the structural formula of:

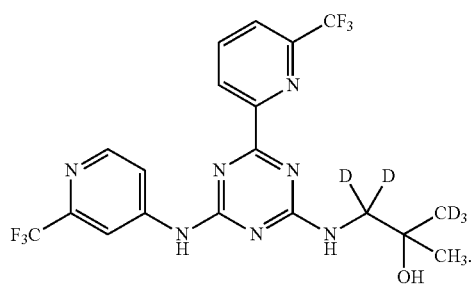

In certain embodiment of the method, the compound has the structural formula of:

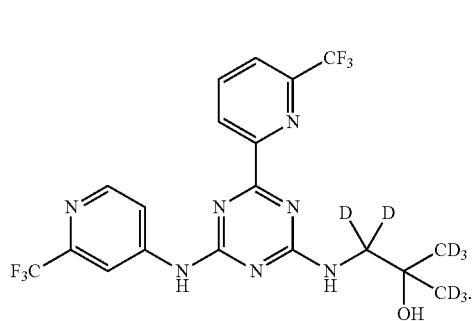

In certain embodiment of the method, the compound has the structural formula of:

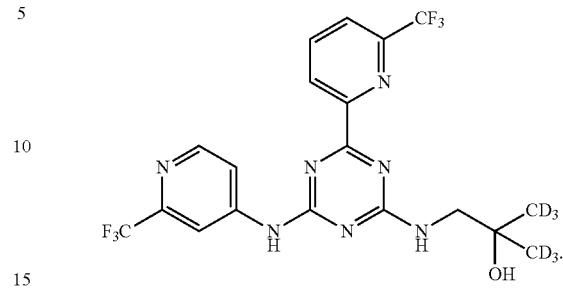

In certain embodiment of the method, the compound has the structural formula of:

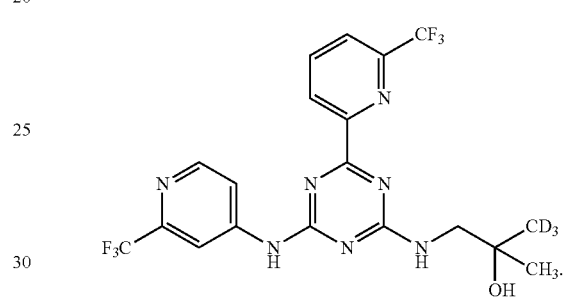

In certain embodiment of the method, the compound has the structural formula of:

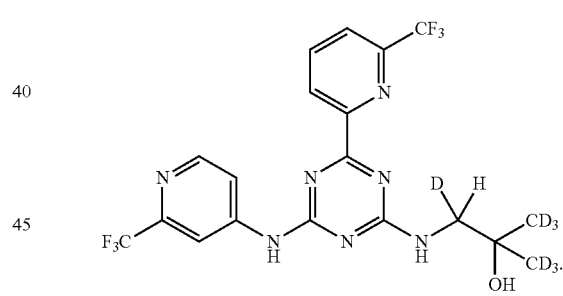

In certain embodiment of the method, the compound has the structural formula of:

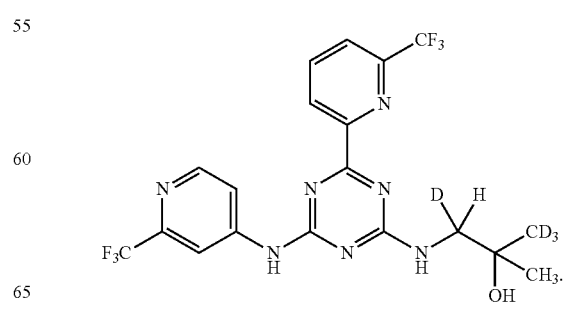

In certain embodiment of the method, the compound has the structural formula of:

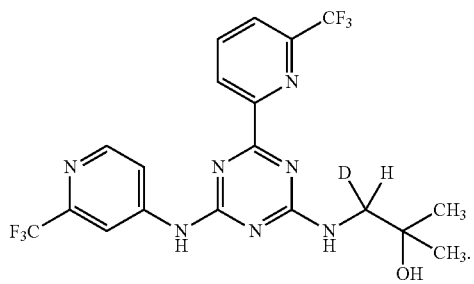

In certain embodiments, the one or more hematologic malignancies include advanced hematologic malignancies, or a related disease or disorder thereof. Exemplary diseases and conditions that may benefit from treatment using the compounds, pharmaceutical composition, unit dosage form and treatment method disclosed herein include any diseases and disorders that harbor an IDH2 mutation, such as acute myelogenous leukemia (AML), myelodysplasia syndrome (MDS), myeloproliferative neoplasms (MPN), myeloproliferative neoplasms (MPN), chronic myelomonocytic leukemia (CMML), B-acute lymphoblastic leukemia (B-ALL), B-acute lymphoblastic leukemia (B-ALL), or lymphoma (e.g., T-cell lymphoma).

In certain embodiments, the diseases and conditions that may be treated with compounds of the invention are solid malignancies.

In certain embodiments, the diseases and conditions that may be treated with compounds of the invention are selected from glioma, chondrosarcoma, intrahepatic cholangiocarcinoma, and angioimmunoblastic T-cell lymphoma cancers.

In certain embodiments, the diseases and conditions that may be treated with compounds of the invention are selected from D-2-hydroxyglutaric aciduria and Ollier and Maffucci syndromes.

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

EXAMPLES

Examples 1-6. Compound Syntheses

Scheme 1 outlines exemplary synthetic procedures.

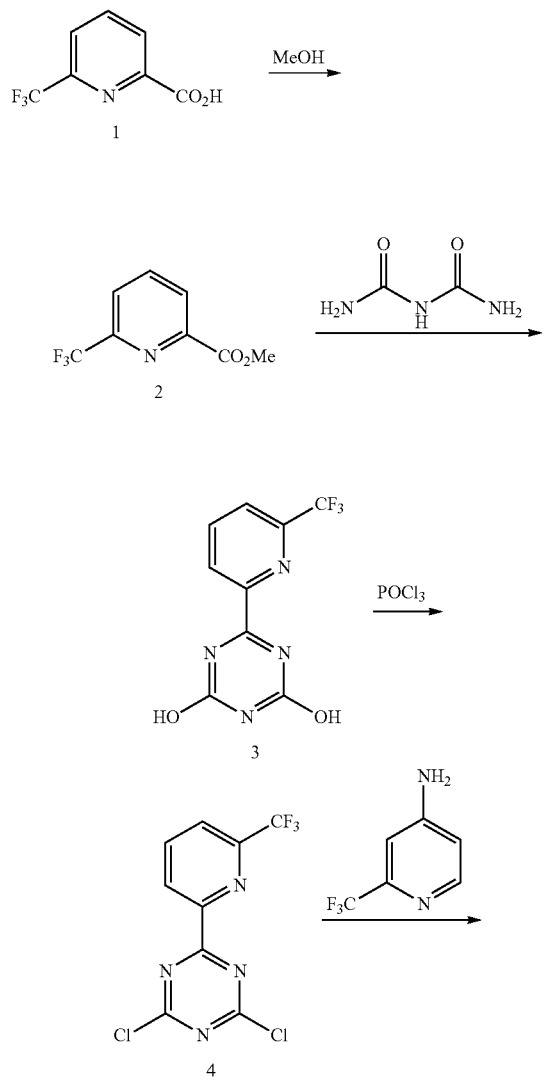

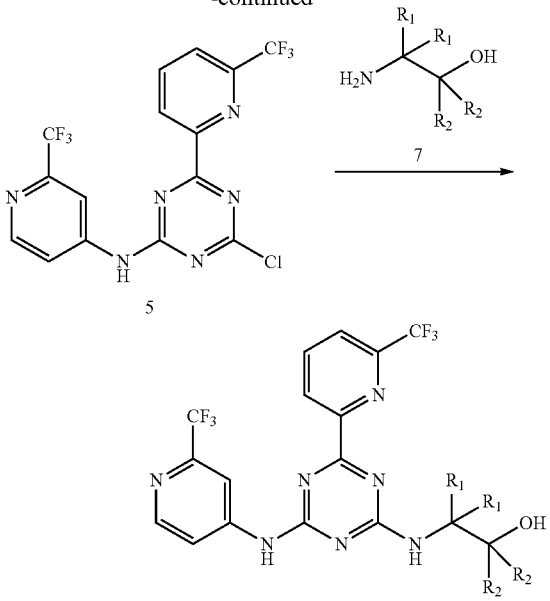

Example 1

Compound 6a: $R_1$=D, $R_2$=$CD_3$.

Example 2

Compound 6b: $R_1$=H, $R_2$=$CD_3$.

Example 3

Compound 6c: $R_1$=D, $R_2$=$CH_3$.

Step 1

Preparation of 6-trifluoromethyl-pyridine-2-carboxylic acid methyl ester (2)

To a solution of 6-trifluoromethyl-pyridine-2-carboxylic acid (22 g, 1 equiv.) in methanol (200 mL) was added concentrated $H_2SO_4$ (0.3 mL). The mixture was stirred at reflux for 14 hours and then cooled to ambient. Solid $NaHCO_3$ (10 g) was added and the suspension was stirred for 30 minutes. The mixture was filtered and the filtrate was concentrated to remove the volatile. The crude product was diluted with ethyl acetated (200 mL) and dried with anhydrous $Na_2SO_4$. The mixture was filtered and concentrated to give 6-trifluoromethyl-pyridine-2-carboxylic acid methyl ester (2) as a waxy solid (21 g).

Step 2

Preparation of 6-(6-trifluoromethyl pyridin-2-yl)-1,3,5-triazine-2,4-dione (3)

To EtOH (320 mL) was added solid Na (2.6 g) in small pieces. The mixture was stirred for 1 hour under nitrogen until all solid dissolved. To this solution was added compound 2 (21 g) and biuret (3.5 g). The mixture was heated to reflux for 1 hour and then cooled. 2 N HCl was added to quench the reaction until pH<7. The solution was then concentrated to give a residue, which was poured to water and EtOAc (200 mL) was added. The precipitated solid was collected by filtration and dried to give 6-(6-trifluoromethyl pyridin-2-yl)-1,3,5-triazine-2,4-dione (3) (8 g).

Step 3

Preparation of 2,4-dichloro-6-(6-trifluoromethyl pyridin-2-yl)-1,3,5-triazine (4)

To a solution of compound 3 (8 g) in POCl$_3$ (50 mL) was added PCl$_5$ (23 g). The mixture was stirred at 100° C. for 1 hour then cooled. The mixture was poured into solid NaHCO$_3$ (200 g) slowly. The mixture was then extracted with ethyl acetated and the organic layer was dried over anhydrous Na$_2$SO$_4$ and concentrated to give 2,4-dichloro-6-(6-trifluoromethyl pyridin-2-yl)-1,3,5-triazine (4) (7.7 g).

Step 4

Preparation of 4-chloro-6-(6-(trifluoromethyl)pyridin-2-yl)-N-(2-(trifluoromethyl)pyridin-4-yl)-1,3,5-triazin-2-amine (5)

To a solution of 2,4-dichloro-6-(6-trifluoromethyl pyridin-2-yl)-1,3,5-triazine (4) (7.7 g) in THF (70 mL) was added 2-(trifluoromethyl)pyridin-4-amine (0.5 g) and NaHCO$_3$ (4.4 g). The mixture was stirred at reflux for 6 hours and cooled. The mixture was directly used without purification in the next step.

Step 5

Compound 6 (e.g., 6a, 6b, 6c). To a solution of 4-chloro-6-(6-(trifluoromethyl)pyridin-2-yl)-N-(2-(trifluoromethyl)pyridin-4-yl)-1,3,5-triazin-2-amine (5) (1.1 g) in anhydrous THF (20 mL) was added amine 7 (1.2 equiv). The mixture was stirred at ambient temperature for 4 hour. After concentration, the residue was purified by silica gel chromatography to give compound 6 (e.g., 6a, 6b, 6c).

Compound 6a: R$_1$=D, R$_2$=CD$_3$. $^1$H NMR (400 MHz, METHANOL-d4) δ 8.62-8.69 (m, 2H), 8.47-8.51 (m, 1H), 8.18-8.22 (m, 1H), 7.96-8.01 (m, 1H), 7.82-7.87 (m, 1H). LC-MS: m/z 482.3 (M+H)+.

Compound 6b: R$_1$=H, R$_2$=CD$_3$. $^1$H NMR (400 MHz, METHANOL-d4) δ 8.62-8.69 (m, 2H), 8.47-8.51 (m, 1H), 8.18-8.22 (m, 1H), 7.96-8.01 (m, 1H), 7.82-7.87 (m, 1H), 3.56-3.63 (m, 2H). LC-MS: m/z 480.0 (M+H)+.

Compound 6c: R$_1$=D, R$_2$=CH$_3$. $^1$H NMR (400 MHz, METHANOL-d4) δ 8.62-8.69 (m, 2H), 8.47-8.51 (m, 1H), 8.18-8.22 (m, 1H), 7.96-8.01 (m, 1H), 7.82-7.87 (m, 1H), 1.26 (s, 6H). LC-MS: m/z 476.3 (M+H)+.

Scheme 2 outlines exemplary synthetic procedures for amine 7 (e.g., 7a, 7b and 7c).

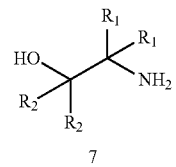

7

Example 4

Compound 7a: R$_1$=D, R$_2$=CD$_3$

Example 5

Compound 7b: R$_1$=H, R$_2$=CD$_3$

Example 6

Compound 7c: R$_1$=D, R$_2$=CH$_3$

Synthesis of Compound 9:

Compound 8 (acetone or acetone-D6 in case of 7a or 7b, 15 mL) was added to a solution of NaHSO$_3$ (25.5 g) in water (50 mL) at 0° C. The mixture was stirred for 1 hour and was added a solution of KCN (16 g) in water (20 mL). The mixture was stirred for 14 hours and was extracted with DCM (100 mL×2). The organic layer was washed with brine and dried over Na$_2$SO$_4$. The mixture was then filtered and the filtrate was concentrated at 0° C. to afford the crude product as a light brown oil (7 g).

Synthesis of Compound 7:

Method A:

Compound 9 (2 g) was added to a LiAlH$_4$ (or LiAlD$_4$ in case of 7a and 7c) suspension in THF at −20° C. The mixture was heated to reflux for 2 hours and stirred at ambient for 14 hours. Water (5 equiv.) was added and the mixture was stirred for 2 hours. The solids were filtered off and the filtrate was concentrated at 0° C. to afford the product as a clear oil (4 g, ~50% purity). 7a: $^1$H NMR (400 MHz, CDCl$_3$) δ 5.00-5.50 (br, 2H).

Method B:

Compound 9 (1 g) was added into a mixture of MeOH and AcOH (1:1, or MeOD and AcOD in case of 7a and 7c). Pd/C (1 g, 10 wt %) was added and the mixture was hydrogenated under 10 atm of H$_2$ (or D$_2$ in case of 7a and 7c) for 12 hours. The mixture was then filtered and the filtrate was added 2 N HCl in dioxane until pH reached 1. The mixture was concentrated to a residue (2.3 g) and neutralized with NaHCO$_3$ before use.

Example 7. Increased Drug Exposure and Half-Life in In Vivo Pharmacokinetic Study on Cynomolgus Monkeys Test compounds were dissolved to yield a final concentration at 0.2 mg/mL. The study conducted formulation analysis by HPLC. The four animals assigned to the study had body weights within ±20% of the mean body weight. The study was conducted in a cross-over matter with four phases to minimize individual difference. The dose level was 1 mg/Kg and the drug was administrated through intravenous (IV) route.

Blood samples (approximately 1.2 mL/sample) were collected from the femintravenous vein at appropriate time points. Samples were placed in tubes containing sodium heparin and stored on ice until centrifuged. Blood samples

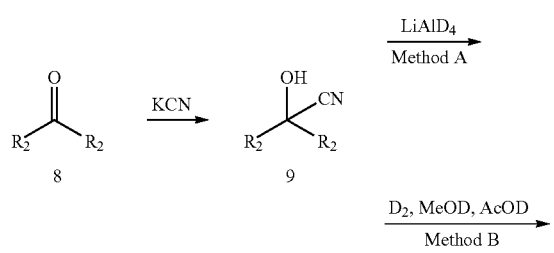

Scheme 2 were collected pre-dose and post-dose at post-dose 2 minutes, 5 minutes, 15 minutes, 30 minutes, 1 hour, 2 hours, 3 hours, 4 hours, 6 hours, 8 hours and 24 hours. The blood samples were centrifuged at approximately 8,000 rpm for 6 minutes at 2-8° C. Plasma samples were then collected and stored frozen at approximately −80° C. until analysis. The bioanalytical work was performed using a LC-MS/MS system.

FIG. 1 shows monkey IV studies of pharmacokinetics comparing enasidenib vs. D8-enasidenib.

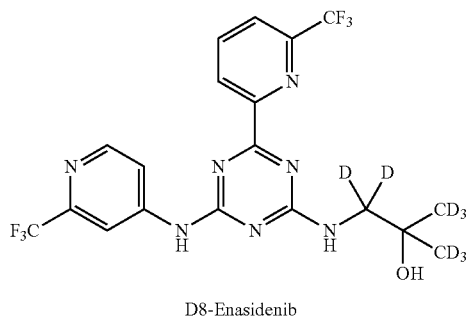 [SMILES: [2H]C([2H])([2H])C(O)(C([2H])([2H])[2H])C([2H])([2H])Nc1nc(Nc2ccnc(C(F)(F)F)c2)nc(-c2cccc(C(F)(F)F)n2)n1]

D8-Enasidenib

TABLE 5

| Improvement on AUC | | | | | |
|---|---|---|---|---|---|
| Animal ID | MK-101 | MK-201 | MK-301 | MK-401 | Average |
| Enasidenib (AG-221) | 7780 | 3438 | 4287 | 5291 | 5199 |
| D8-Enasidenib | 8970 | 5814 | 10296 | 6534 | 7904 |
| AUC Differentiation (%) | 15.3 | 69.1 | 140 | 23.5 | 62.0 |

Based on in vivo pharmacokinetic study on monkey, D8-enasidenib showed superior DMPK property over enasidenib by selectively modifying the structure. The increased drug exposure based on the area under the curve (AUC) and half-life affords enhanced pharmacological effect and leads to better drug efficacy. Efficacious dosage level can be reduced allowing minimized toxicity and side effects.

Example 8. Drug Metabolism Study of Enasidenib and D8-Enasidenib with Rat and Human Microsomes This study was carried out to evaluate drug metabolism of the test compounds by rat and human microsomes. Test compounds were incubated with liver microsomes of rat (BioreclamationIVT, Lot# NNK) and human (BioreclamationIVT, Lot# HPG) at 37° C. for 60 minutes. The substrate compound concentration was at 10 µM and final protein concentration in incubation mixtures was 1 mg/mL. Reaction was stopped by adding three fold acetonitrile to the reaction mixture. The samples were vortexed and centrifuged to precipitate the proteins. The supernatants were transferred to clean tubes for drying under a stream of $N_2$. The dried residues were reconstituted with 30% acetonitrile. Aliquots were injected into an LC/UV/MS system for metabolite ID and profiling. The LC/UV/MS system was Agilent 1100 HPLC (pumps, autosampler and PDA) interfaced to LTQ ion trap mass spectrometer (ThermoFinnigan). HPLC column was Luna C18(2) column, 250×2.0 mm, 5

The HPLC mobile phase gradient system were water and acetonitrile with 0.05% trifluoroacetic acid in both solvents.

The experimental data indicated oxidation (hydroxylation) and de-alkylation were two of major metabolism paths for enasidenib and D8-enasidenib. For oxidation on aromatic ring, the molecular weights of hydroxylation products were the original ones plus an oxygen (+16). The C—H bond of enasidenib is replaced by C—OH. For oxidation on side chains, the molecular weights of hydroxylation products are different for enasidenib vs. D8-enasidenib. For enasidenib, the C—H bond is also replaced by C—OH and the difference in molecular weights is 16. However, since D8-enasidenib loses a deuterium due to hydroxylation (C-D is replaced by C—OH), the difference of its molecular weight to the original is 15 (that is +O+H−D=15). (FIG. 2) Thus, the hydroxylation products for aromatic ring and side chain for enasidenib and D8-enasidenib can be identified.

Figure 3:
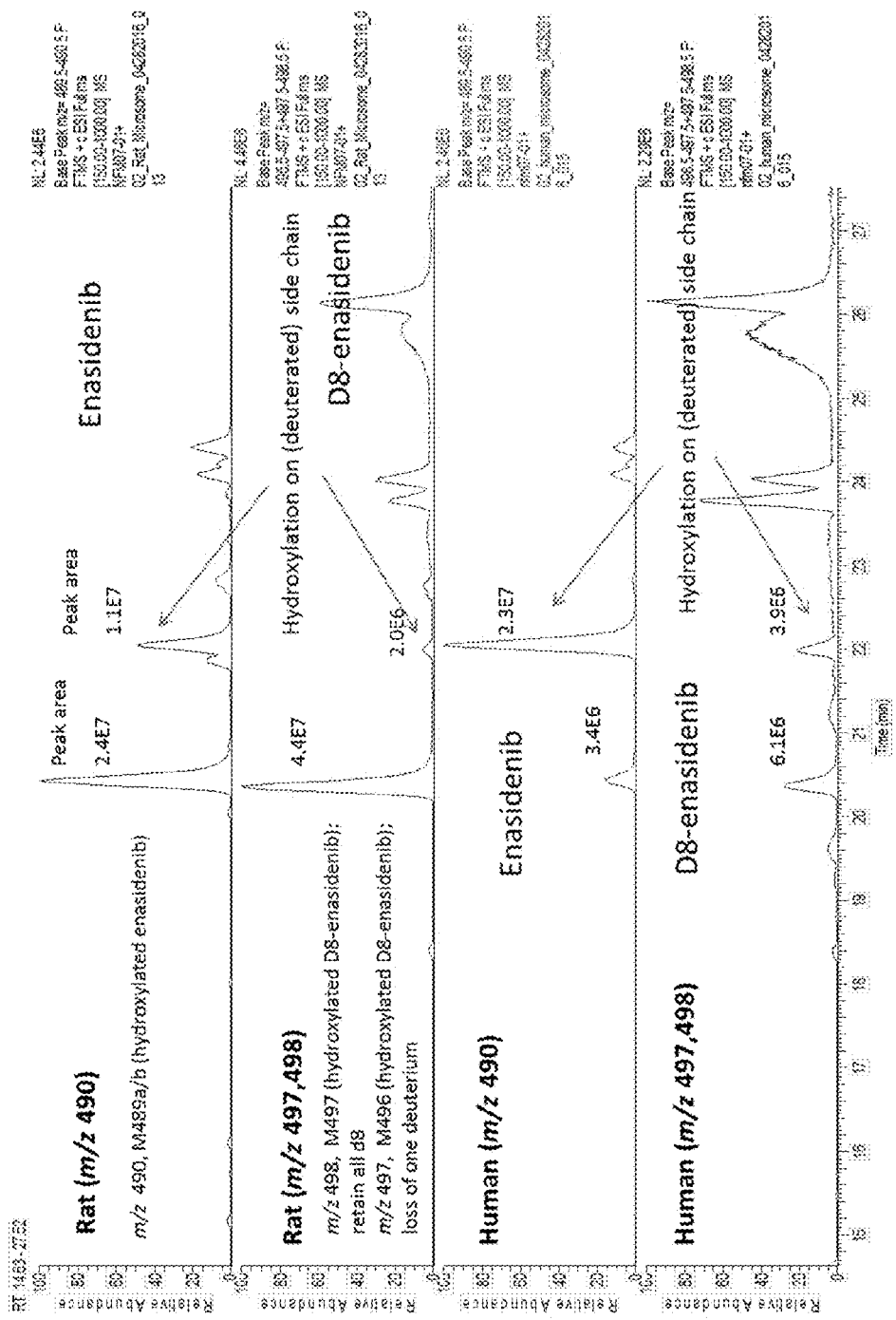
FIG. 3 shows exemplary data on oxidation of enasidenib and D8-enasidenib (1:1) in the presence of liver microsomes fortified with NADPH (LC/MS XIC m/z 490,497,498).
Figure 4:
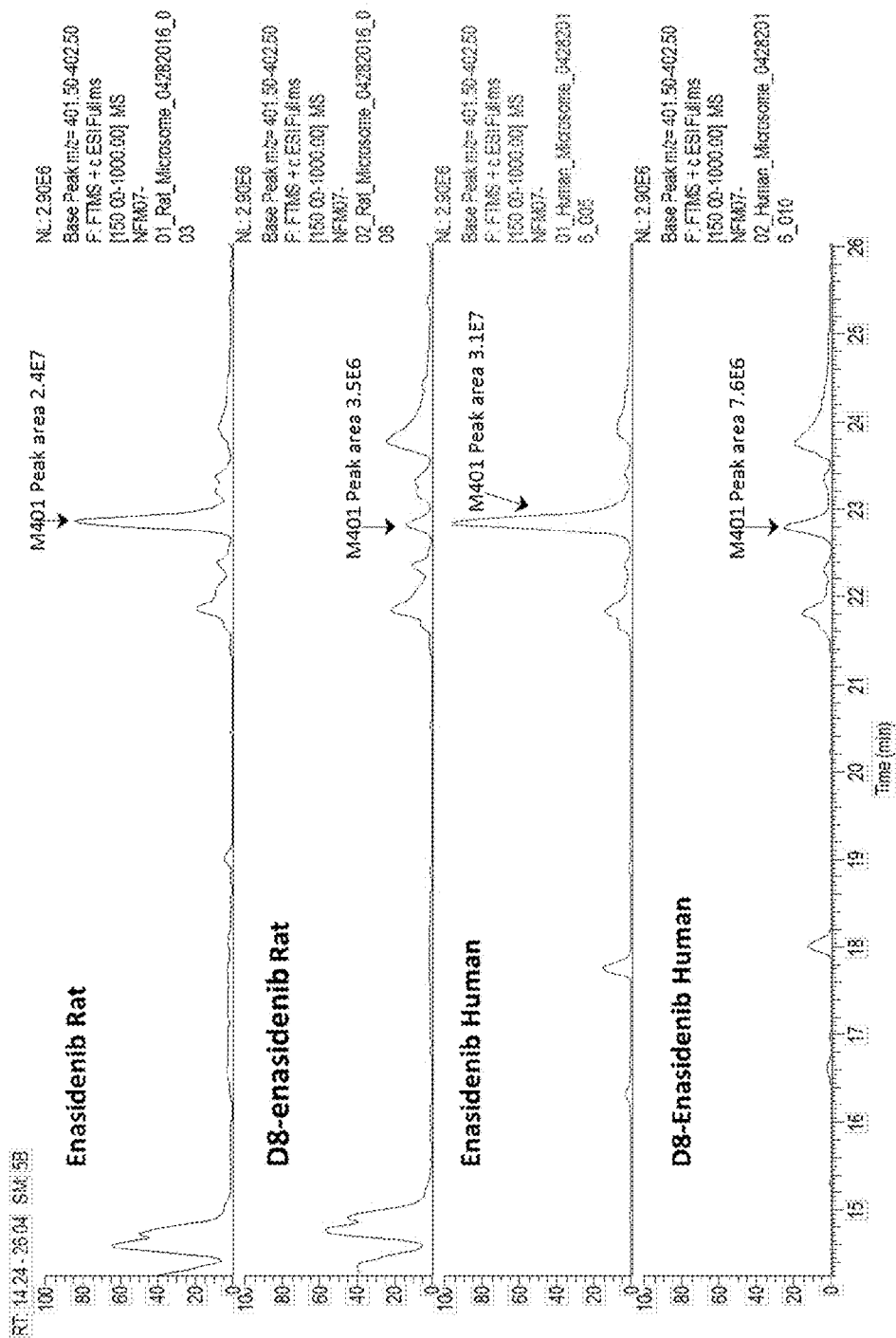
FIG. 4 shows exemplary data on N-dealkylated metabolite of enasidenib and D8-enasidenib in the presence of liver microsomes fortified with NADPH (LC/MS XIC m/z 402).

As the analysis in FIG. 3, the formation of hydroxylation product on aromatic ring (Retention time: 20.4 minutes) was similar while on the side chain the hydroxylation (Retention time: 22.0 minutes) of D8-enasidenib was greatly reduced when comparing to that of enasidenib. As shown in FIG. 4, the formation of de-alkylation product was significantly slowed down for D8-enasidenib. Both results from oxidation and de-alkylation analysis supported superior DMPK property of D8-enasidenib, which was demonstrated in monkey study.

Example 9. Pharmacokinetic and Drug Metabolism Study of Enasidenib and D8-Enasidenib with Human Hepatocyte This study was carried out to evaluate the stability of the test compounds upon metabolism by cryopreserved human hepatocytes. Test compounds were incubated with 10-donor pooled human hepatocytes to evaluate the stability of the test compounds upon metabolism by cryopreserved human hepatocytes.

Cryopreserved hepatocytes represent a well-accepted experimental system for the evaluation of drug properties including metabolic stability, metabolite identification, drug-drug interaction potential, and hepatotoxic potential. The test compounds were administered in vitro directly or through a solvent compatible with the test system.

The No-Cells (NC) Negative Control consisted of the addition of test compound but no hepatocytes added. These samples represented possible chemical degradation and/or adsorbance to surfaces and "stickiness" of a particular compound. No Cells control was also run at similar time points (i.e. T=0 minute, 30 minutes, 60 minutes, 120 minutes, 240 minutes and 360 minutes). The no cell control was carried out in incubation media and was run as single incubation as per the request of the sponsor.

Pooled cryopreserved hepatocytes were thawed in a 37° C. water bath and placed on ice. The thawed hepatocytes were recovered using Universal Cryopreserved Recovery Medium™ (UCRM™) and centrifuged at 100×g for 5 minutes to remove residual cryopreservants. The hepatocyte pellet were re-suspended in William's E based medium HIM (In Vitro ADMET LABORATORIES, Inc., Maryland). Viability and cell concentration were determined based on trypan blue exclusion using a hemacytometer. The cell suspension was adjusted to $1.11 \times 10^6$ cells per mL and placed on ice until use.

The final reaction mixture for hepatocyte metabolism consisted of HIM, hepatocytes at $1\times10^6$ cells per mL and the test compound or negative controls.

The study was designed such that a reference compound (enasidenib) was used along with one another test compound per group. The final concentration of reference compound and the test compound at the initiation of incubation was 2 μM. Each test compound including reference compound was prepared as 20,000× stock in DMSO at concentration of 40 mM. Each test compound was mixed with reference compound in equal volume to prepare a combined 10,000× DMSO stock of 20 mM each. This DMSO stock was diluted 1000× in HIM to prepare a 10× dosing stock of 20 μM. This dosing stock was diluted to 2 μM upon addition to medium containing hepatocytes or blank medium.

Incubation of the hepatocytes with 2 μM test compound+reference compound was performed in triplicates in an incubator maintained at 37° C. and humidified atmosphere of 5% $CO_2$ and 95% balanced air for time periods of 0, 30, 60, 120, 240 and 360 minutes and concentrations of the hepatocytes at $1\times10^6$ cells per mL. Negative controls included samples in the absence of hepatocytes (incubation media) but with 2 μM test compound+reference compound only at the same six time points. These controls were conducted under identical conditions. Total reaction volume was 500 μL (0.450 mL hepatocytes suspension+0.050 mL incubation buffer media with 10× test compound or positive control). All samples except negative control were run in triplicates.

Reactions were initiated with the addition of 0.050 mL of the test chemical in buffer (mixing-up and down motion of the multichannel pipet to mix well test compound with incubation media mixture), and placed in a 37° C. incubator. At designated time points 50 μL of samples were collected from each treatment group followed by addition of 100 μL of ice-cold acetonitrile containing 1 μg/mL carbutamide (internal standard). Internal standards were added to all the samples.

One concentration (2 μM) of the test compound+reference compound was used in all incubations. The reference compound at 2 μM in each group served as positive control. After incubation, the reaction was terminated. The total mixture after termination was stored frozen for LCMS analysis.

Figure 5:
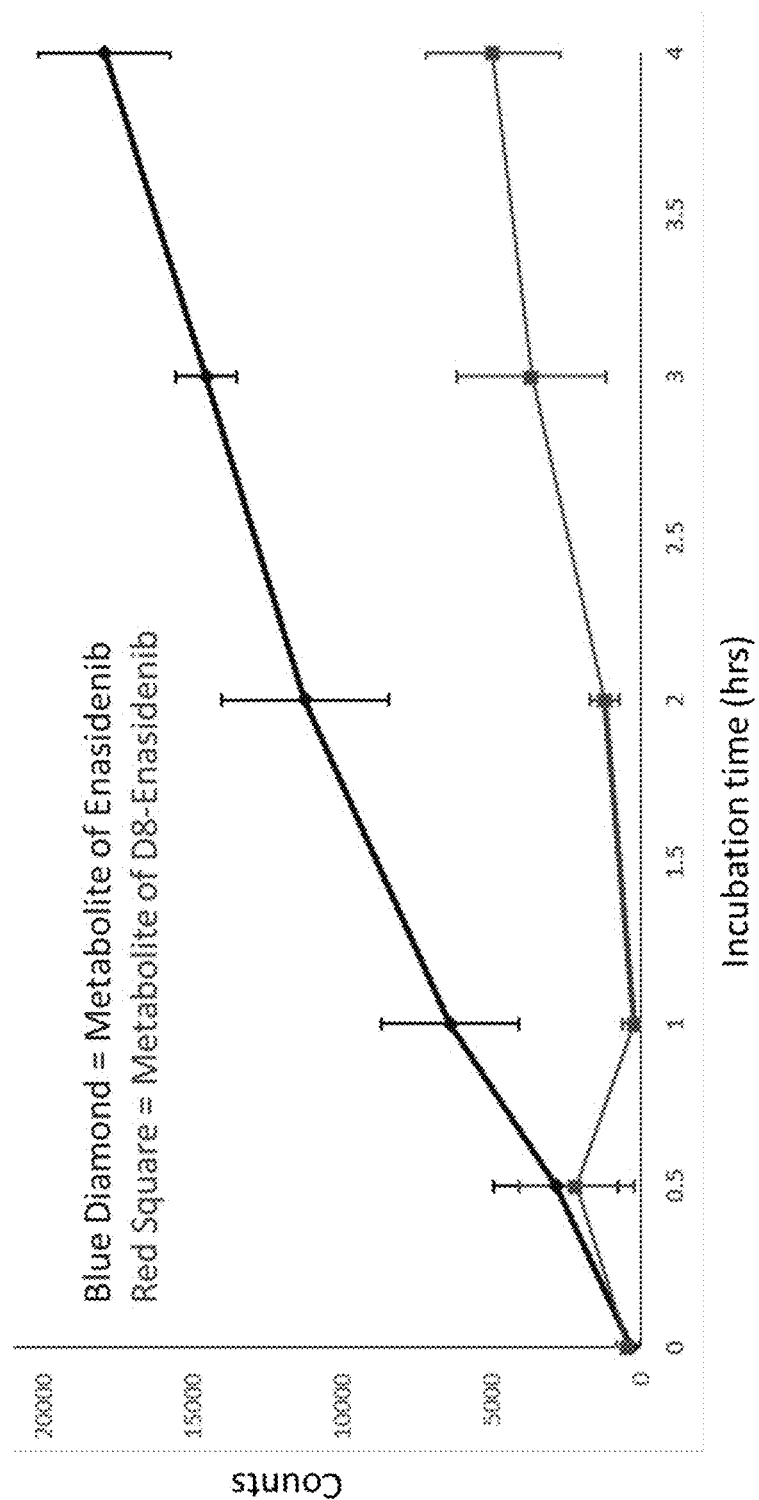
FIG. 5 shows exemplary data on human hepatocyte study of oxidation metabolite (enasidenib vs. D8-enasidenib).

Quantitative experimental results indicated that for the selectively deuterated compound D8-enasidenib both formation of oxidation metabolite and de-alkylation product decreased. (FIG. 5) After a four-hour incubation, the concentration of the metabolite with one oxygen at side chain (M496, FIG. 2) of D8-enasidenib was reduced by 72% comparing with that of enasidenib (M489b, FIG. 2). The de-alkylation product decreased 22% comparing with enasidenib. These results further supported the observation from in vivo monkey pharmacokinetic studies that D8-enasidenib showed superior DMPK property than enasidenib.

The same experiment was performed for D2-enasidenib and D6-enasidenib.

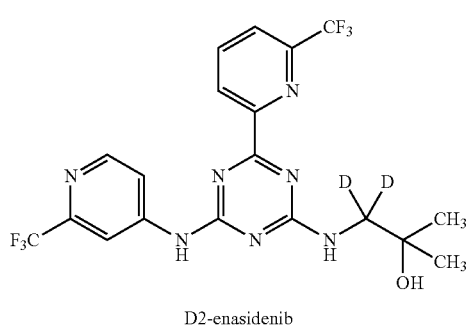

D2-enasidenib

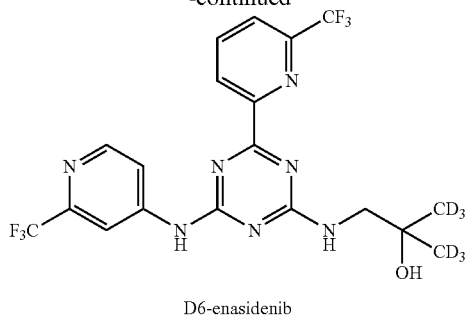

D6-enasidenib

Figure 2:
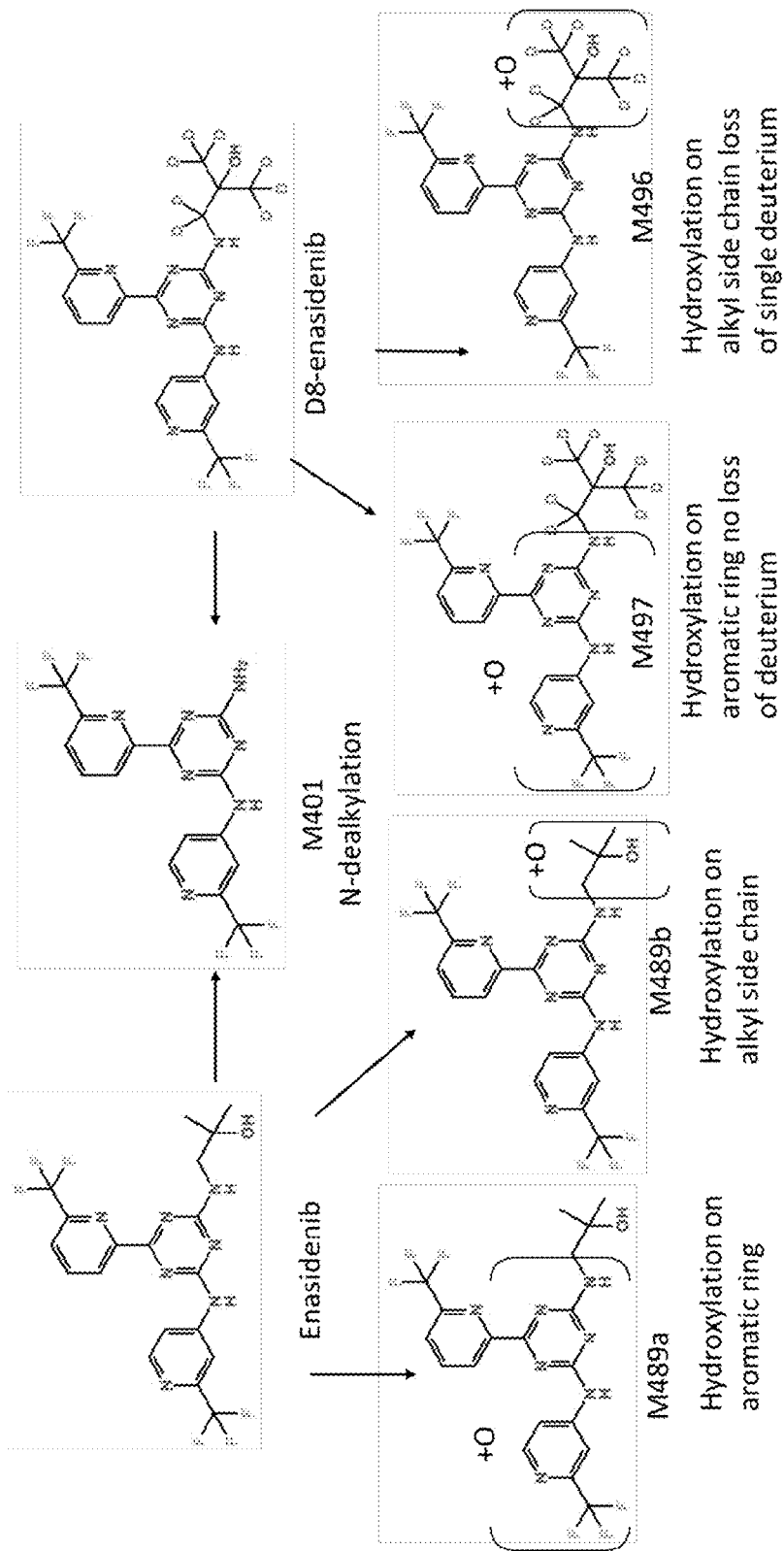
FIG. 2 shows the proposed metabolic pathways of enasidenib and D8-enasidenib.

After a four-hour incubation, the concentration of the metabolite with one oxygen at side chain (M496, FIG. 2) of D6-enasidenib was reduced by 71% comparing with that of enasidenib (M489b, FIG. 2). The de-alkylation product for D2-enasidenib was decreased 28% comparing with enasidenib. Both results showed the significant improvement of DMPK properties for D2-enasidenib and D6-enasidenib.

Example 10. Bioactivity Study—IC50 Measurement Against IDH2 R140Q

Compounds were tested in 10-dose IC50 mode with 3-fold serial dilution at a starting concentration of 10 μM. Substrate and co-factor were 8000 μM α-Ketoglutarate and 15 μM NADPH (reduced form of nicotinamide adenine dinucleotide phosphate). The reaction was carried out by mixing compound solutions with enzyme (IDH2 R140Q) and pre-incubated for 60 minutes. Then a four-fold substrate mixture was delivered to initiate the reaction. The solutions were incubated for 45 minutes at room temperature. Detection was performed using diaphorase and resazurin and measured in Envision (Perkin-Elmer). (Ex/Em=535/590 nm). The experimental result showed that the deuterated compound D8-enasidenib had similar IC50 to enasidenib. The value for D8-enasidenib (IC50=3.60E-07) is within 10% of that of enansidenib (IC50=3.62E-07).

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the following description, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A compound having the structural formula of:

(VI)

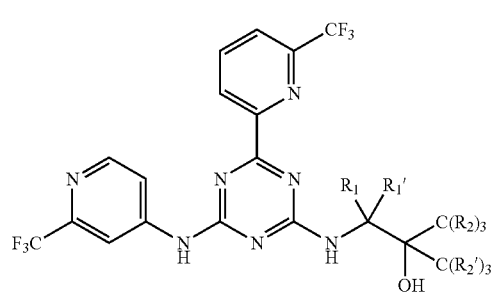

wherein each of $R_1$, $R_{1'}$, $R_2$ and $R_{2'}$ is independently selected from H and D; provided that at least one of $R_1$, $R_{1'}$, $R_2$ and $R_{2'}$ is D, or a pharmaceutically acceptable form thereof.

2. The compound of claim 1, wherein each of $R_1$ and $R_{1'}$ is D and each of $R_2$ and $R_{2'}$ is H, having the structural formula of:

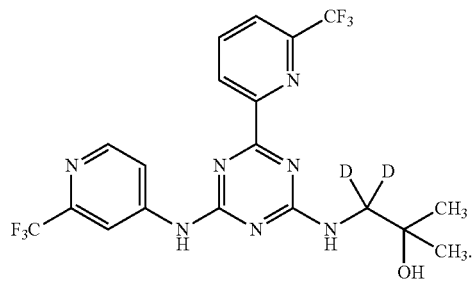 [SMILES: [2H]C([2H])([2H])C(O)(C([2H])([2H])[2H])C([2H])([2H])Nc1nc(Nc2ccnc(C(F)(F)F)c2)nc(-c2cccc(C(F)(F)F)n2)n1]

3. The compound of claim 1, wherein each of $R_1$ and $R_{1'}$ is D and each of $R_2$ and $R_{2'}$ is D, having the structural formula of:

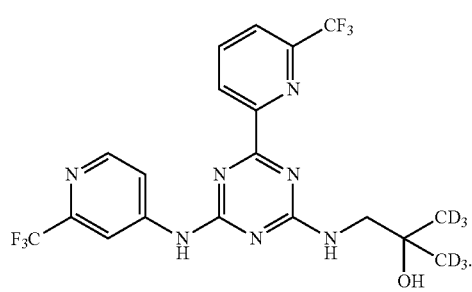

4. The compound of claim 1, wherein each of $R_1$ and $R_{1'}$ is H and each of $R_2$ and $R_{2'}$ is D, having the structural formula of:

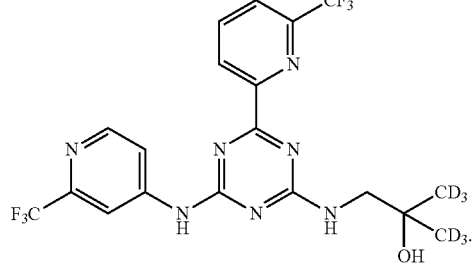

5. A pharmaceutical composition comprising a compound having the structural formula of:

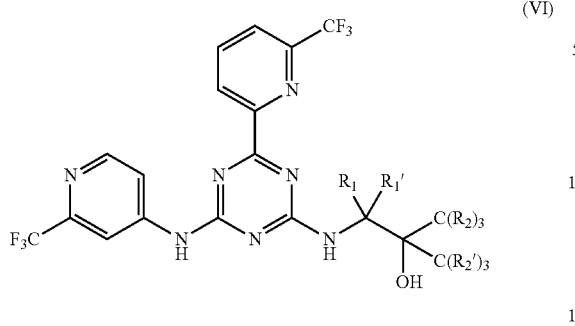

(VI)

wherein each of $R_1$, $R_{1'}$, $R_2$ and $R_{2'}$ is independently selected from H and D; provided that at least one of $R_1$, $R_{1'}$, $R_2$ and $R_{2'}$ is D, or a pharmaceutically acceptable form thereof, effective to treat acute myelogenous leukemia, or a related disease or disorder thereof, in a mammal, including a human, and a pharmaceutically acceptable excipient, carrier, or diluent.

6. The pharmaceutical composition of claim 5, wherein each of $R_1$ and $R_{1'}$ is D and each of $R_2$ and $R_{2'}$ is H, having the structural formula of:

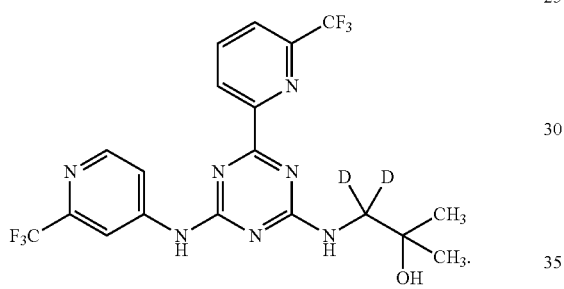

7. The pharmaceutical composition of claim 5, wherein each of $R_1$ and $R_{1'}$ is D and each of $R_2$ and $R_{2'}$ is D, having the structural formula of:

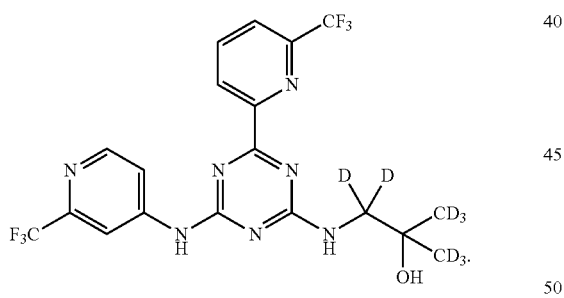

8. The pharmaceutical composition of claim 5, wherein each of $R_1$ and $R_{1'}$ is H and each of $R_2$ and $R_{2'}$ is D, having the structural formula of:

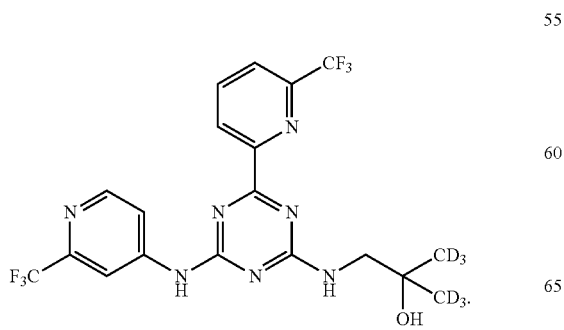

9. A unit dosage form comprising the pharmaceutical composition of claim 5.

10. The unit dosage form of claim 9, wherein the compound is selected from

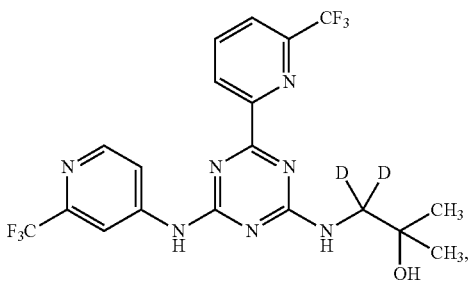

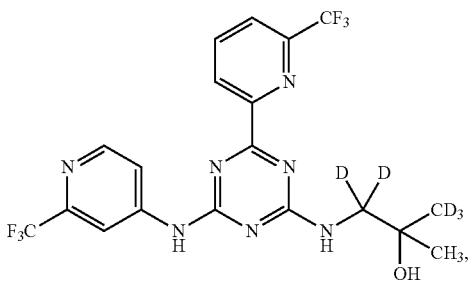

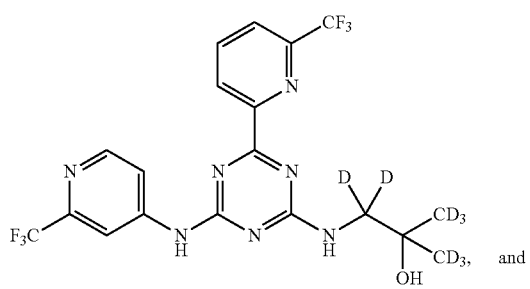

and

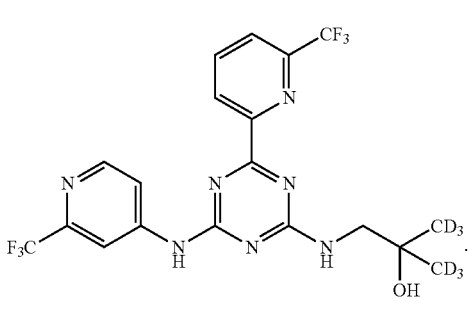 [SMILES: [2H]C([2H])([2H])C(O)(CNc1nc(Nc2ccnc(C(F)(F)F)c2)nc(-c2cccc(C(F)(F)F)n2)n1)C([2H])([2H])[2H]]

11. A method for treating acute myelogenous leukemia, comprising:
  administering to a subject in need thereof a pharmaceutical composition comprising compound having the formula of:

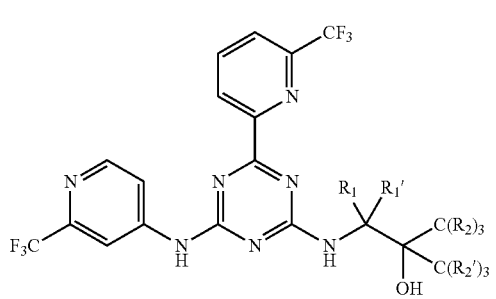

(VI)

wherein each of $R_1$, $R_{1'}$, $R_2$ and $R_{2'}$ is independently selected from H and D; provided that at least one of $R_1$, $R_{1'}$, $R_2$ and $R_{2'}$ is D, or a pharmaceutically acceptable form thereof, effective to treat acute myelogenous leukemia, or a related disease or disorder thereof, in a mammal, including a human, and a pharmaceutically acceptable excipient, carrier, or diluent.

12. The method of claim 11, wherein each of $R_1$ and $R_{1'}$ is D and each of $R_2$ and $R_{2'}$ is H, having the structural formula of:

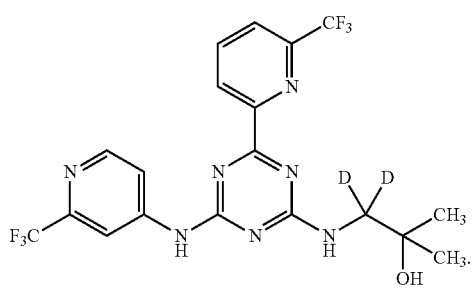

13. The method of claim 11, wherein each of $R_1$ and $R_{1'}$ is D and each of $R_2$ and $R_{2'}$ is D, having the structural formula of:

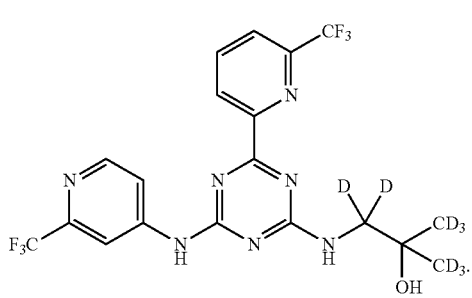 [SMILES: [2H]C([2H])([2H])C(O)(C([2H])([2H])[2H])C([2H])([2H])Nc1nc(Nc2ccnc(C(F)(F)F)c2)nc(-c2cccc(C(F)(F)F)n2)n1]

14. The method of claim 11, wherein each of $R_1$ and $R_{1'}$ is H and each of $R_2$ and $R_{2'}$ is D, having the structural formula of:

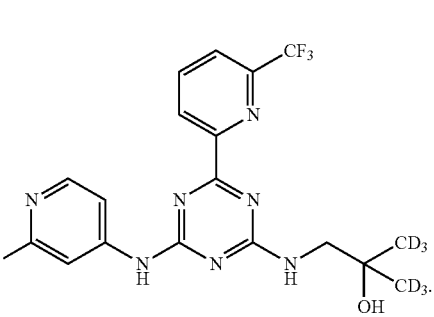

* * * * *